(12) United States Patent
Yamamoto et al.

(10) Patent No.: US 8,187,853 B2
(45) Date of Patent: May 29, 2012

(54) β-GALACTOSIDE-α2,6-SIALYLTRANS-FERASE, A GENE ENCODING THEREOF, AND A METHOD FOR ENHANCING ENZYME ACTIVITY

(75) Inventors: Takeshi Yamamoto, Iwata (JP); Yoshimitsu Takakura, Iwata (JP); Toshiki Mine, Iwata (JP); Yoko Hamada, Iwata (JP); Hitomi Kajiwara, Iwata (JP); Masako Ichikawa, Iwata (JP); Hiroshi Tsukamoto, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 394 days.

(21) Appl. No.: 12/529,496

(22) PCT Filed: Mar. 3, 2008

(86) PCT No.: PCT/JP2008/053748
§ 371 (c)(1),
(2), (4) Date: Sep. 1, 2009

(87) PCT Pub. No.: WO2008/108325
PCT Pub. Date: Sep. 12, 2008

(65) Prior Publication Data
US 2010/0112616 A1 May 6, 2010

(30) Foreign Application Priority Data

Mar. 2, 2007 (JP) .................................. 2007-053270
Mar. 23, 2007 (JP) .................................. 2007-076798

(51) Int. Cl.
*C12N 9/10* (2006.01)
(52) U.S. Cl. ........................... 435/193; 435/15; 536/23.2
(58) Field of Classification Search .................. 435/193, 435/15; 536/23.2
See application file for complete search history.

(56) References Cited

U.S. PATENT DOCUMENTS 5,827,714 A 10/1998 Yamamoto et al.
6,255,094 B1 7/2001 Yamamoto et al.

FOREIGN PATENT DOCUMENTS

| EP | 0915163 A1 | 5/1999 |
|---|---|---|
| JP | 8-154673 A | 6/1996 |
| JP | 10-234373 A | 9/1998 |
| WO | WO 98/38315 A1 | 8/1998 |
| WO | WO 2006/054333 A1 | 5/2006 |

OTHER PUBLICATIONS

Extended European Search Report dated May 10, 2010 for European application No. 08721168.6 (PCT/JP2008053748).
Hamada et al., "Characteristics of a Sialyltransferase Produced by Marine Bacterium *Photobacterium leiognathi* JT-SHIZ-145", Japan Society for Bioscience, Biotechnology, and Agrochemistry Taikai Koen Yoshishu, Mar. 5, 2007, vol. 2007, p. 149.
Hamamoto et al., "Two Step Single Primer Mediated Polymerase Chain Reaction,[1] Application to Cloning of Putative Mouse, β-Galactoside α2,6-Sialyltransferase cDNA", Bioorg. Med. Chem., (1993), vol. 1, No. 2, pp. 141-145.
Paulson et al., "Enzymatic Properties of β-D-Galactoside α2->6 Sialyltransfenase from Bovine Colostrum", J. Biol. Chem, (1977), vol. 252, No. 7, pp. 2363-2371.
Weinstein et al., "Primary Structure of β-Galactoside α2,6-Sialyltransferase", J. Biol. Chem., (1987), vol. 262, No. 36, pp. 17735-17743.
Yamamoto et al., "A β-galactoside α2,6-Sialyltransferase Produced by a Marine Bacterium, *Photobacterium leiognathi* JT-SHIZ-145, is active at pH 6", Glycobiology, (2007), vol. 17, No. 11, pp. 1167-1174.
Yamamoto et al., "Purification and Characterization of a Marine Bacterial β-Galactoside α2,6-Sialyltransferase from *Photobacterium damsels* JT0160", J. Biochem, (1996), vol. 120, pp. 104-110.

*Primary Examiner* — Tekchand Saidha
(74) *Attorney, Agent, or Firm* — Birch, Stewart, Kolasch & Birch, LLP

(57) ABSTRACT

The present invention provides an extremely useful and novel β-galactoside-α2,6-sialyltransferase having an optimum reaction pH in a neutral to alkaline range, and a nucleic acid encoding the sialyltransferase. The present invention further provides a vector carrying a nucleic acid encoding the sialyltransferase, and a host cell transformed with the vector, as well as a method for producing a recombinant β-galactoside-α2,6-sialyltransferase.

10 Claims, 5 Drawing Sheets

SEQUENCE LISTING

```
<160> NUMBER OF SEQ ID NOS: 9

<210> SEQ ID NO 1
<211> LENGTH: 1494
<212> TYPE: DNA
<213> ORGANISM: Photobacterium leiognathi
<220> FEATURE:
<221> NAME/KEY: CDS
<222> LOCATION: (1)..(1494)

<400> SEQUENCE: 1 atg aaa aga ata ttt tgt tta gtc tct gct att tta tta tca gca tgt      48
Met Lys Arg Ile Phe Cys Leu Val Ser Ala Ile Leu Leu Ser Ala Cys
1               5                   10                  15 aat gat aat cag aat aca gta gat gta gtt gta tct act gtg aat gat      96
Asn Asp Asn Gln Asn Thr Val Asp Val Val Val Ser Thr Val Asn Asp
            20                  25                  30 aac gtt att gaa aat aat act tac caa gtt aaa ccc att gat act cca     144
Asn Val Ile Glu Asn Asn Thr Tyr Gln Val Lys Pro Ile Asp Thr Pro
        35                  40                  45 act act ttt gat tcc tat tct tgg ata caa aca tgc ggt act cca ata     192
Thr Thr Phe Asp Ser Tyr Ser Trp Ile Gln Thr Cys Gly Thr Pro Ile
    50                  55                  60 tta aaa gac gat gag aag tac tct ttg agt ttt gac ttt gtt gca cct     240
Leu Lys Asp Asp Glu Lys Tyr Ser Leu Ser Phe Asp Phe Val Ala Pro
65                  70                  75                  80 gag tta gat caa gat gaa aaa ttc tgc ttt gag ttt act ggt gat gtt     288
Glu Leu Asp Gln Asp Glu Lys Phe Cys Phe Glu Phe Thr Gly Asp Val
                85                  90                  95 gat ggt aag cgt tat gtt acc caa acg aat tta act gtt gtt gcc cca     336
Asp Gly Lys Arg Tyr Val Thr Gln Thr Asn Leu Thr Val Val Ala Pro
            100                 105                 110 aca cta gaa gta tat gtg gat cat gca tca ttg cca tca tta cag cag     384
Thr Leu Glu Val Tyr Val Asp His Ala Ser Leu Pro Ser Leu Gln Gln
        115                 120                 125
```

| | | |
|---|---|---|
| tta atg aaa ata atc caa cag aaa aat gag tat tca cag aat gag cgc<br>Leu Met Lys Ile Ile Gln Gln Lys Asn Glu Tyr Ser Gln Asn Glu Arg<br>130                           135                   140 | | 432 |
| ttt att tct tgg gga cga att aga ctt aca gaa gat aat gca gaa aaa<br>Phe Ile Ser Trp Gly Arg Ile Arg Leu Thr Glu Asp Asn Ala Glu Lys<br>145                  150                 155                160 | | 480 |
| tta aat gcc cat ata tat cca tta gct gga aat aat aca tca caa gaa<br>Leu Asn Ala His Ile Tyr Pro Leu Ala Gly Asn Asn Thr Ser Gln Glu<br>                  165                 170                175 | | 528 |
| ctt gta gat gca gtt att gac tat gct gac tct aaa aat cga tta aat<br>Leu Val Asp Ala Val Ile Asp Tyr Ala Asp Ser Lys Asn Arg Leu Asn<br>              180                 185                190 | | 576 |
| cta gag ctt aat acg aat acg ggg cac tct ttt cgt aac atc gct cca<br>Leu Glu Leu Asn Thr Asn Thr Gly His Ser Phe Arg Asn Ile Ala Pro<br>195                         200                 205 | | 624 |
| ata tta cgt gca aca tca tca aag aat aat ata ttg atc tca aat att<br>Ile Leu Arg Ala Thr Ser Ser Lys Asn Asn Ile Leu Ile Ser Asn Ile<br>          210                 215                220 | | 672 |
| aat cta tac gat gat ggt tca gct gaa tat gtt agc ctt tat aac tgg<br>Asn Leu Tyr Asp Asp Gly Ser Ala Glu Tyr Val Ser Leu Tyr Asn Trp<br>225                       230                 235                240 | | 720 |
| aaa gat act gac aat aaa tct caa aaa tta tct gat agt ttt tta gtt<br>Lys Asp Thr Asp Asn Lys Ser Gln Lys Leu Ser Asp Ser Phe Leu Val<br>                  245                 250                255 | | 768 |
| ctt aaa gat tat tta aat ggt att tct tcg gaa aaa ccg aat ggt att<br>Leu Lys Asp Tyr Leu Asn Gly Ile Ser Ser Glu Lys Pro Asn Gly Ile<br>              260                 265                270 | | 816 |
| tac agt ata tat aac tgg cat cag cta tat cat tca agt tac tac ttt<br>Tyr Ser Ile Tyr Asn Trp His Gln Leu Tyr His Ser Ser Tyr Tyr Phe<br>                275                 280                285 | | 864 |
| ctt cga aag gat tac cta act gtt gaa act aag tta cat gat tta aga<br>Leu Arg Lys Asp Tyr Leu Thr Val Glu Thr Lys Leu His Asp Leu Arg<br>290                       295                 300 | | 912 |
| gaa tat tta ggt ggt tcc tta aag cag atg tca tgg gat act ttt tcg<br>Glu Tyr Leu Gly Gly Ser Leu Lys Gln Met Ser Trp Asp Thr Phe Ser<br>305                       310                 315                320 | | 960 |
| caa tta tca aaa ggt gat aaa gaa cta ttt tta aat att gtt ggg ttt<br>Gln Leu Ser Lys Gly Asp Lys Glu Leu Phe Leu Asn Ile Val Gly Phe<br>                  325                 330                335 | | 1008 |
| gac caa gaa aaa tta cag caa gaa tat caa caa tct gaa ttg cct aat<br>Asp Gln Glu Lys Leu Gln Gln Glu Tyr Gln Gln Ser Glu Leu Pro Asn<br>              340                 345                350 | | 1056 |
| ttt gtt ttc aca ggg acg aca aca tgg gct ggt ggt gaa act aaa gaa<br>Phe Val Phe Thr Gly Thr Thr Thr Trp Ala Gly Gly Glu Thr Lys Glu<br>355                       360                 365 | | 1104 |
| tat tat gct caa cag cag gta aat gtt gtt aat aat gca ata aat gag<br>Tyr Tyr Ala Gln Gln Gln Val Asn Val Val Asn Asn Ala Ile Asn Glu<br>370                       375                 380 | | 1152 |
| aca agt cct tac tat cta ggt aga gag cat gat ctt ttc ttt aaa ggc<br>Thr Ser Pro Tyr Tyr Leu Gly Arg Glu His Asp Leu Phe Phe Lys Gly<br>385                       390                 395                400 | | 1200 |
| cat cca aga gga gga att att aat gat att att tta ggc agt ttt aat<br>His Pro Arg Gly Gly Ile Ile Asn Asp Ile Ile Leu Gly Ser Phe Asn<br>                  405                 410                415 | | 1248 |
| aat atg att gat att cca gct aag gta tca ttt gaa gta ttg atg atg<br>Asn Met Ile Asp Ile Pro Ala Lys Val Ser Phe Glu Val Leu Met Met<br>              420                 425                430 | | 1296 |
| aca ggg atg cta cct gat act gtt gga ggt att gca agc tct ttg tat<br>Thr Gly Met Leu Pro Asp Thr Val Gly Gly Ile Ala Ser Ser Leu Tyr<br>435                       440                 445 | | 1344 |

```
ttt tca ata cca gct gaa aaa gta agt ttt att gta ttt aca tcg tct    1392
Phe Ser Ile Pro Ala Glu Lys Val Ser Phe Ile Val Phe Thr Ser Ser
    450             455                 460 gac act att aca gat aga gag gac gca tta aaa tcg cct tta gtt caa    1440
Asp Thr Ile Thr Asp Arg Glu Asp Ala Leu Lys Ser Pro Leu Val Gln
465             470                 475                 480 gta atg atg aca ttg ggt att gta aaa gaa aaa gat gtt cta ttt tgg    1488
Val Met Met Thr Leu Gly Ile Val Lys Glu Lys Asp Val Leu Phe Trp
                485                 490                 495 tgc tga                                                             1494
Cys

<210> SEQ ID NO 2
<211> LENGTH: 497
<212> TYPE: PRT
<213> ORGANISM: Photobacterium leiognathi

<400> SEQUENCE: 2

Met Lys Arg Ile Phe Cys Leu Val Ser Ala Ile Leu Leu Ser Ala Cys
1               5                   10                  15

Asn Asp Asn Gln Asn Thr Val Asp Val Val Ser Thr Val Asn Asp
            20                  25                  30

Asn Val Ile Glu Asn Asn Thr Tyr Gln Val Lys Pro Ile Asp Thr Pro
        35                  40                  45

Thr Thr Phe Asp Ser Tyr Ser Trp Ile Gln Thr Cys Gly Thr Pro Ile
    50                  55                  60

Leu Lys Asp Asp Glu Lys Tyr Ser Leu Ser Phe Asp Phe Val Ala Pro
65                  70                  75                  80

Glu Leu Asp Gln Asp Glu Lys Phe Cys Phe Glu Phe Thr Gly Asp Val
                85                  90                  95

Asp Gly Lys Arg Tyr Val Thr Gln Thr Asn Leu Thr Val Val Ala Pro
            100                 105                 110

Thr Leu Glu Val Tyr Val Asp His Ala Ser Leu Pro Ser Leu Gln Gln
        115                 120                 125

Leu Met Lys Ile Ile Gln Gln Lys Asn Glu Tyr Ser Gln Asn Glu Arg
    130                 135                 140

Phe Ile Ser Trp Gly Arg Ile Arg Leu Thr Glu Asp Asn Ala Glu Lys
145                 150                 155                 160

Leu Asn Ala His Ile Tyr Pro Leu Ala Gly Asn Asn Thr Ser Gln Glu
                165                 170                 175

Leu Val Asp Ala Val Ile Asp Tyr Ala Asp Ser Lys Asn Arg Leu Asn
            180                 185                 190

Leu Glu Leu Asn Thr Asn Thr Gly His Ser Phe Arg Asn Ile Ala Pro
        195                 200                 205

Ile Leu Arg Ala Thr Ser Ser Lys Asn Asn Ile Leu Ile Ser Asn Ile
    210                 215                 220

Asn Leu Tyr Asp Asp Gly Ser Ala Glu Tyr Val Ser Leu Tyr Asn Trp
225                 230                 235                 240

Lys Asp Thr Asp Asn Lys Ser Gln Lys Leu Ser Asp Ser Phe Leu Val
                245                 250                 255

Leu Lys Asp Tyr Leu Asn Gly Ile Ser Ser Glu Lys Pro Asn Gly Ile
            260                 265                 270

Tyr Ser Ile Tyr Asn Trp His Gln Leu Tyr His Ser Ser Tyr Tyr Phe
        275                 280                 285

Leu Arg Lys Asp Tyr Leu Thr Val Glu Thr Lys Leu His Asp Leu Arg
    290                 295                 300
```

```
Glu Tyr Leu Gly Gly Ser Leu Lys Gln Met Ser Trp Asp Thr Phe Ser
305                 310                 315                 320

Gln Leu Ser Lys Gly Asp Lys Glu Leu Phe Leu Asn Ile Val Gly Phe
            325                 330                 335

Asp Gln Glu Lys Leu Gln Gln Glu Tyr Gln Gln Ser Glu Leu Pro Asn
                340                 345                 350

Phe Val Phe Thr Gly Thr Thr Thr Trp Ala Gly Gly Glu Thr Lys Glu
                355                 360                 365

Tyr Tyr Ala Gln Gln Val Asn Val Val Asn Asn Ala Ile Asn Glu
370                 375                 380

Thr Ser Pro Tyr Tyr Leu Gly Arg Glu His Asp Leu Phe Phe Lys Gly
385                 390                 395                 400

His Pro Arg Gly Gly Ile Ile Asn Asp Ile Ile Leu Gly Ser Phe Asn
                405                 410                 415

Asn Met Ile Asp Ile Pro Ala Lys Val Ser Phe Glu Val Leu Met Met
                420                 425                 430

Thr Gly Met Leu Pro Asp Thr Val Gly Gly Ile Ala Ser Ser Leu Tyr
            435                 440                 445

Phe Ser Ile Pro Ala Glu Lys Val Ser Phe Ile Val Phe Thr Ser Ser
450                 455                 460

Asp Thr Ile Thr Asp Arg Glu Asp Ala Leu Lys Ser Pro Leu Val Gln
465                 470                 475                 480

Val Met Met Thr Leu Gly Ile Val Lys Glu Lys Asp Val Leu Phe Trp
                485                 490                 495

Cys

<210> SEQ ID NO 3
<211> LENGTH: 1452
<212> TYPE: DNA
<213> ORGANISM: Artificial Sequence
<220> FEATURE:
<223> OTHER INFORMATION: A nucleotide encoding a fragment of
      beta-sialyltransferase from photobacterium leiognathi
<220> FEATURE:
<221> NAME/KEY: CDS
<222> LOCATION: (1)..(1452)

<400> SEQUENCE: 3 atg tgt aat gat aat cag aat aca gta gat gta gtt gta tct act gtg      48
Met Cys Asn Asp Asn Gln Asn Thr Val Asp Val Val Val Ser Thr Val
1               5                   10                  15 aat gat aac gtt att gaa aat aat act tac caa gtt aaa ccc att gat      96
Asn Asp Asn Val Ile Glu Asn Asn Thr Tyr Gln Val Lys Pro Ile Asp
                20                  25                  30 act cca act act ttt gat tcc tat tct tgg ata caa aca tgc ggt act     144
Thr Pro Thr Thr Phe Asp Ser Tyr Ser Trp Ile Gln Thr Cys Gly Thr
            35                  40                  45 cca ata tta aaa gac gat gag aag tac tct ttg agt ttt gac ttt gtt     192
Pro Ile Leu Lys Asp Asp Glu Lys Tyr Ser Leu Ser Phe Asp Phe Val
        50                  55                  60 gca cct gag tta gat caa gat gaa aaa ttc tgc ttt gag ttt act ggt     240
Ala Pro Glu Leu Asp Gln Asp Glu Lys Phe Cys Phe Glu Phe Thr Gly
65                  70                  75                  80 gat gtt gat ggt aag cgt tat gtt acc caa acg aat tta act gtt gtt     288
Asp Val Asp Gly Lys Arg Tyr Val Thr Gln Thr Asn Leu Thr Val Val
                85                  90                  95 gcc cca aca cta gaa gta tat gtg gat cat gca tca ttg cca tca tta     336
Ala Pro Thr Leu Glu Val Tyr Val Asp His Ala Ser Leu Pro Ser Leu
                100                 105                 110
```

```
cag cag tta atg aaa ata atc caa cag aaa aat gag tat tca cag aat    384
Gln Gln Leu Met Lys Ile Ile Gln Gln Lys Asn Glu Tyr Ser Gln Asn
        115                 120                 125 gag cgc ttt att tct tgg gga cga att aga ctt aca gaa gat aat gca    432
Glu Arg Phe Ile Ser Trp Gly Arg Ile Arg Leu Thr Glu Asp Asn Ala
    130                 135                 140 gaa aaa tta aat gcc cat ata tat cca tta gct gga aat aat aca tca    480
Glu Lys Leu Asn Ala His Ile Tyr Pro Leu Ala Gly Asn Asn Thr Ser
145                 150                 155                 160 caa gaa ctt gta gat gca gtt att gac tat gct gac tct aaa aat cga    528
Gln Glu Leu Val Asp Ala Val Ile Asp Tyr Ala Asp Ser Lys Asn Arg
                165                 170                 175 tta aat cta gag ctt aat acg aat acg ggg cac tct ttt cgt aac atc    576
Leu Asn Leu Glu Leu Asn Thr Asn Thr Gly His Ser Phe Arg Asn Ile
            180                 185                 190 gct cca ata tta cgt gca aca tca tca aag aat aat ata ttg atc tca    624
Ala Pro Ile Leu Arg Ala Thr Ser Ser Lys Asn Asn Ile Leu Ile Ser
        195                 200                 205 aat att aat cta tac gat gat ggt tca gct gaa tat gtt agc ctt tat    672
Asn Ile Asn Leu Tyr Asp Asp Gly Ser Ala Glu Tyr Val Ser Leu Tyr
210                 215                 220 aac tgg aaa gat act gac aat aaa tct caa aaa tta tct gat agt ttt    720
Asn Trp Lys Asp Thr Asp Asn Lys Ser Gln Lys Leu Ser Asp Ser Phe
225                 230                 235                 240 tta gtt ctt aaa gat tat tta aat ggt att tct tcg gaa aaa ccg aat    768
Leu Val Leu Lys Asp Tyr Leu Asn Gly Ile Ser Ser Glu Lys Pro Asn
                245                 250                 255 ggt att tac agt ata tat aac tgg cat cag cta tat cat tca agt tac    816
Gly Ile Tyr Ser Ile Tyr Asn Trp His Gln Leu Tyr His Ser Ser Tyr
            260                 265                 270 tac ttt ctt cga aag gat tac cta act gtt gaa act aag tta cat gat    864
Tyr Phe Leu Arg Lys Asp Tyr Leu Thr Val Glu Thr Lys Leu His Asp
        275                 280                 285 tta aga gaa tat tta ggt ggt tcc tta aag cag atg tca tgg gat act    912
Leu Arg Glu Tyr Leu Gly Gly Ser Leu Lys Gln Met Ser Trp Asp Thr
    290                 295                 300 ttt tcg caa tta tca aaa ggt gat aaa gaa cta ttt tta aat att gtt    960
Phe Ser Gln Leu Ser Lys Gly Asp Lys Glu Leu Phe Leu Asn Ile Val
305                 310                 315                 320 ggg ttt gac caa gaa aaa tta cag caa gaa tat caa caa tct gaa ttg   1008
Gly Phe Asp Gln Glu Lys Leu Gln Gln Glu Tyr Gln Gln Ser Glu Leu
                325                 330                 335 cct aat ttt gtt ttc aca ggg acg aca aca tgg gct ggt ggt gaa act   1056
Pro Asn Phe Val Phe Thr Gly Thr Thr Thr Trp Ala Gly Gly Glu Thr
            340                 345                 350 aaa gaa tat tat gct caa cag cag gta aat gtt gtt aat aat gca ata   1104
Lys Glu Tyr Tyr Ala Gln Gln Gln Val Asn Val Val Asn Asn Ala Ile
        355                 360                 365 aat gag aca agt cct tac tat cta ggt aga gag cat gat ctt ttc ttt   1152
Asn Glu Thr Ser Pro Tyr Tyr Leu Gly Arg Glu His Asp Leu Phe Phe
    370                 375                 380 aaa ggc cat cca aga gga gga att att aat gat att att tta ggc agt   1200
Lys Gly His Pro Arg Gly Gly Ile Ile Asn Asp Ile Ile Leu Gly Ser
385                 390                 395                 400 ttt aat aat atg att gat att cca gct aag gta tca ttt gaa gta ttg   1248
Phe Asn Asn Met Ile Asp Ile Pro Ala Lys Val Ser Phe Glu Val Leu
                405                 410                 415 atg atg aca ggg atg cta cct gat act gtt gga ggt att gca agc tct   1296
Met Met Thr Gly Met Leu Pro Asp Thr Val Gly Gly Ile Ala Ser Ser
            420                 425                 430
```

```
ttg tat ttt tca ata cca gct gaa aaa gta agt ttt att gta ttt aca    1344
Leu Tyr Phe Ser Ile Pro Ala Glu Lys Val Ser Phe Ile Val Phe Thr
        435                 440                 445 tcg tct gac act att aca gat aga gag gac gca tta aaa tcg cct tta    1392
Ser Ser Asp Thr Ile Thr Asp Arg Glu Asp Ala Leu Lys Ser Pro Leu
    450                 455                 460 gtt caa gta atg atg aca ttg ggt att gta aaa gaa aaa gat gtt cta    1440
Val Gln Val Met Met Thr Leu Gly Ile Val Lys Glu Lys Asp Val Leu
465                 470                 475                 480 ttt tgg tgc tga                                                    1452
Phe Trp Cys <210> SEQ ID NO 4
<211> LENGTH: 483
<212> TYPE: PRT
<213> ORGANISM: Artificial Sequence
<220> FEATURE:
<223> OTHER INFORMATION: Synthetic Construct

<400> SEQUENCE: 4

Met Cys Asn Asp Asn Gln Asn Thr Val Asp Val Val Ser Thr Val
1               5                   10                  15

Asn Asp Asn Val Ile Glu Asn Asn Thr Tyr Gln Val Lys Pro Ile Asp
            20                  25                  30

Thr Pro Thr Thr Phe Asp Ser Tyr Ser Trp Ile Gln Thr Cys Gly Thr
        35                  40                  45

Pro Ile Leu Lys Asp Asp Glu Lys Tyr Ser Leu Ser Phe Asp Phe Val
    50                  55                  60

Ala Pro Glu Leu Asp Gln Asp Glu Lys Phe Cys Phe Glu Phe Thr Gly
65                  70                  75                  80

Asp Val Asp Gly Lys Arg Tyr Val Thr Gln Thr Asn Leu Thr Val Val
                85                  90                  95

Ala Pro Thr Leu Glu Val Tyr Val Asp His Ala Ser Leu Pro Ser Leu
            100                 105                 110

Gln Gln Leu Met Lys Ile Ile Gln Gln Lys Asn Glu Tyr Ser Gln Asn
        115                 120                 125

Glu Arg Phe Ile Ser Trp Gly Arg Ile Arg Leu Thr Glu Asp Asn Ala
    130                 135                 140

Glu Lys Leu Asn Ala His Ile Tyr Pro Leu Ala Gly Asn Asn Thr Ser
145                 150                 155                 160

Gln Glu Leu Val Asp Ala Val Ile Asp Tyr Ala Asp Ser Lys Asn Arg
                165                 170                 175

Leu Asn Leu Glu Leu Asn Thr Asn Thr Gly His Ser Phe Arg Asn Ile
            180                 185                 190

Ala Pro Ile Leu Arg Ala Thr Ser Ser Lys Asn Asn Ile Leu Ile Ser
        195                 200                 205

Asn Ile Asn Leu Tyr Asp Asp Gly Ser Ala Glu Tyr Val Ser Leu Tyr
    210                 215                 220

Asn Trp Lys Asp Thr Asp Asn Lys Ser Gln Lys Leu Ser Asp Ser Phe
225                 230                 235                 240

Leu Val Leu Lys Asp Tyr Leu Asn Gly Ile Ser Ser Glu Lys Pro Asn
                245                 250                 255

Gly Ile Tyr Ser Ile Tyr Asn Trp His Gln Leu Tyr His Ser Ser Tyr
            260                 265                 270

Tyr Phe Leu Arg Lys Asp Tyr Leu Thr Val Glu Thr Lys Leu His Asp
        275                 280                 285

Leu Arg Glu Tyr Leu Gly Gly Ser Leu Lys Gln Met Ser Trp Asp Thr
```

|     |     |     |     |     |     |     |     |     |     |
| --- | --- | --- | --- | --- | --- | --- | --- | --- | --- |
|     | 290 |     |     | 295 |     |     | 300 |     |     |

Phe Ser Gln Leu Ser Lys Gly Asp Lys Glu Leu Phe Leu Asn Ile Val
305             310             315             320

Gly Phe Asp Gln Glu Lys Leu Gln Gln Glu Tyr Gln Gln Ser Glu Leu
        325             330             335

Pro Asn Phe Val Phe Thr Gly Thr Thr Thr Trp Ala Gly Gly Glu Thr
        340             345             350

Lys Glu Tyr Tyr Ala Gln Gln Val Asn Val Asn Asn Ala Ile
        355             360             365

Asn Glu Thr Ser Pro Tyr Tyr Leu Gly Arg Glu His Asp Leu Phe Phe
370             375             380

Lys Gly His Pro Arg Gly Gly Ile Ile Asn Asp Ile Leu Gly Ser
385             390             395             400

Phe Asn Asn Met Ile Asp Ile Pro Ala Lys Val Ser Phe Glu Val Leu
        405             410             415

Met Met Thr Gly Met Leu Pro Asp Thr Val Gly Gly Ile Ala Ser Ser
        420             425             430

Leu Tyr Phe Ser Ile Pro Ala Glu Lys Val Ser Phe Ile Val Phe Thr
        435             440             445

Ser Ser Asp Thr Ile Thr Asp Arg Glu Asp Ala Leu Lys Ser Pro Leu
        450             455             460

Val Gln Val Met Met Thr Leu Gly Ile Val Lys Glu Lys Asp Val Leu
465             470             475             480

Phe Trp Cys

<210> SEQ ID NO 5
<211> LENGTH: 22
<212> TYPE: DNA
<213> ORGANISM: Artificial Sequence
<220> FEATURE:
<223> OTHER INFORMATION: Synthetic primer: SHIZ145 26 N1

<400> SEQUENCE: 5
gccatcatta cagcagttaa tg                                      22

<210> SEQ ID NO 6
<211> LENGTH: 22
<212> TYPE: DNA
<213> ORGANISM: Artificial Sequence
<220> FEATURE:
<223> OTHER INFORMATION: Synthetic primer: SHIZ145 26 N2

<400> SEQUENCE: 6
tgagtattca cagaatgagc gc                                      22

<210> SEQ ID NO 7
<211> LENGTH: 29
<212> TYPE: DNA
<213> ORGANISM: Artificial Sequence
<220> FEATURE:
<223> OTHER INFORMATION: Synthetic primer: SHIZ145 N0 BspHI

<400> SEQUENCE: 7
aaagggtcat gaaaagaata ttttgttta                               29

<210> SEQ ID NO 8
<211> LENGTH: 33
<212> TYPE: DNA
<213> ORGANISM: Artificial Sequence
<220> FEATURE:
<223> OTHER INFORMATION: Synthetic primer: SHIZ145 C0 Hind

```
<400> SEQUENCE: 8
atgagcaagc tttcagcacc aaaatagaac atc                              33

<210> SEQ ID NO 9
<211> LENGTH: 30
<212> TYPE: DNA
<213> ORGANISM: Artificial Sequence
<220> FEATURE:
<223> OTHER INFORMATION: Synthetic primer: SHIZ145 N1 Pci

<400> SEQUENCE: 9
tatacatgtg taatgataat cagaatacag                                  30
```

β-GALACTOSIDE-α2,6-SIALYLTRANSFERASE, A GENE ENCODING THEREOF, AND A METHOD FOR ENHANCING ENZYME ACTIVITY

TECHNICAL FIELD

The present invention relates to a novel β-galactoside-α2,6-sialyltransferase, a gene encoding the enzyme, and a method for producing the enzyme using a microorganism which has been transformed with the gene encoding the enzyme.

BACKGROUND ART

Glycosyltransferases are enzymes involved in in vivo biosynthesis of sugar chains on glycoproteins, glycolipids and the like (hereinafter referred to as "complex carbohydrates"). Their reaction products, i.e., sugar chains on complex carbohydrates have very important functions in the body. For example, sugar chains have been shown to be important molecules primarily in mammalian cells, which play a role in cell-cell and cell-extracellular matrix signaling and serve as tags for complex carbohydrates during differentiation and/or development.

Erythropoietin, a hormone for blood erythrocyte production, can be presented as an example where sugar chains are applied. Naturally-occurring erythropoietin is disadvantageous in that it has a short-lasting effect. Although erythropoietin is inherently a glycoprotein, further attempts have been made to add new sugar chains onto erythropoietin, as a result of which recombinant erythropoietin proteins with an extended in vivo life span have been developed and produced and are now commercially available. In the future, there will be increasing development of such products in which sugar chains are added or modified, including pharmaceuticals and functional foods. Thus, it is required to develop a means for freely synthesizing and producing sugar chains. In particular, the development of glycosyltransferases is increasing in importance as one of the most efficient means.

Until now, about 150 or more glycosyltransferase genes have been isolated from eukaryotic organisms including humans, mice, rats and yeast. Moreover, these genes have been expressed in host cells such as CHO cells or *E. coli* cells to produce proteins having glycosyltransferase activity. On the other hand, about 20 to 30 types of glycosyltransferase genes have also been isolated from bacteria which are prokaryotic organisms. Moreover, proteins having glycosyltransferase activity have been expressed in recombinant production systems using *E. coli* and identified for their substrate specificity and/or various enzymatic properties.

Sialic acid is often located at the nonreducing termini of sugar chains and is therefore regarded as a very important sugar in terms of allowing sugar chains to exert their functions. For this reason, sialyltransferase is one of the most in demand enzymes among glycosyltransferases. As to β-galactoside-α2,6-sialyltransferases and their genes, many reports have been issued for those derived from animals, particularly mammals (Hamamoto, T., et al., Bioorg. Med. Chem., 1, 141-145 (1993); Weinstein, J., et al., J. Biol. Chem., 262, 17735-17743 (1987)). However, such animal-derived enzymes are very expensive because they are difficult to purify and hence cannot be obtained in large amounts. Moreover, such enzymes have a problem in that they have poor stability as enzymes. In contrast, as to bacterial β-galactoside-α2,6-sialyltransferases and their genes, reports have been issued for those isolated from microorganisms belonging to *Photobacterium damselae* (International Publication No. WO98/38315; U.S. Pat. No. 6,255,094; Yamamoto, T., et al., J. Biochem., 120, 104-110 (1996)).

Various mammalian and bacterial sialyltransferases previously known are reported to have an optimum reaction pH in an acidic range, e.g., between pH 5 and 6 (Paulson, J. C. et al., J. Biol. Chem., 252, 2363-2371 (1977), Yamamoto, T., et al., J. Biochem., 120, 104-110 (1996)). It is widely known that sialic acid attached to simple sugar chains or complex carbohydrate sugar chains on various glycoproteins, glycolipids and the like is gradually degraded under acidic conditions. Moreover, CMP-sialic acid, which is a glycosyl donor substrate of sialyltransferase and is extremely high in price, is known to be rapidly degraded under acidic conditions, but extremely stable under alkaline conditions. Thus, in the case of using sialyltransferase for transfer of sialic acid to various complex carbohydrates or sugar chains, there is a demand for sialyltransferase having an optimum reaction pH in a neutral to alkaline range, in terms of post-reaction stability and storage properties of sialic acid-containing sugar chains and also in terms of efficient use of CMP-sialic acid for use in sialic acid transfer reaction.

Patent Document 1: International Publication No. WO98/38315

Patent Document 2: U.S. Pat. No. 6,255,094

Non-patent Document 1: Hamamoto, T., et al., Bioorg. Med. Chem., 1, 141-145 (1993)

Non-patent Document 2: Weinstein, J., et al., J. Biol. Chem., 262, 17735-17743 (1987)

Non-patent Document 3: Yamamoto, T., et al., J. Biochem., 120, 104-110 (1996)

Non-patent Document 4: Paulson, J. C. et al., J. Biol. Chem., 252, 2363-2371 (1977)

DISCLOSURE OF THE INVENTION

Problems to be Solved by the Invention

A problem to be solved by the present invention is to provide a novel β-galactoside-α2,6-sialyltransferase derived from a microorganism belonging to the genus *Photobacterium* of the family Vibrionaceae, and a gene encoding the same. More specifically, the present invention aims to provide a novel β-galactoside-α2,6-sialyltransferase having an optimum reaction pH in a neutral to alkaline range, and a gene encoding the same.

Another problem to be solved by the present invention is to provide a method for high production of the β-galactoside-α2,6-sialyltransferase of the present invention by gene recombination technology using a gene encoding this enzyme.

Yet another problem to be solved by the present invention is to provide a method for increasing the efficiency of sialic acid transfer reaction mediated by the β-galactoside-α2,6-sialyltransferase of the present invention.

Means for Solving the Problems

As a result of extensive and intensive efforts made to separate and characterize 4,000 or more microbial strains from all areas of Japan, the inventors of the present invention have found a strain producing β-galactoside-α2,6-sialyltransferase activity from among strains of microorganisms belonging to the genus *Photobacterium*. The inventors have then cloned a novel α2,6-sialyltransferase gene from this strain by using as a probe the DNA of a known β-galactoside-α2,6-sialyltransferase gene from *Photobacterium damselae*. As a result of expressing this novel gene in *E. coli* cells, the inventors have found that this gene encodes a protein having β-galactoside-α2,6-sialyltransferase activity, and that the encoded enzyme protein has an optimum reaction pH of 7 to 9.5. As a result of further efforts to purify and analyze in detail this novel recombinant enzyme, the inventors have also found that this recombinant enzyme efficiently transfers sialic acid in α2,6 linkage to monosaccharides or galactose, N-acetylgalactosamine or other residues in sugar chains, thereby completing the present invention. The present invention provides a novel β-galactoside-α2,6-sialyltransferase having an optimum reaction pH in a neutral to alkaline range, and a nucleic acid encoding the same, as well as a method for producing the sialyltransferase.

The present invention will now be illustrated in detail below.

β-Galactoside-α2,6-sialyltransferase

The present invention provides a novel β-galactoside-α2, 6-sialyltransferase. As used herein, the term "β-galactoside-α2,6-sialyltransferase" is intended to mean a protein having the ability to transfer sialic acid from cytidine monophosphate (CMP)-sialic acid to the 6-position of a galactose residue in complex carbohydrate sugar chains or free sugar chains, to the 6-position of galactose present in oligosaccharides such as lactose or N-acetyllactosamine, or to the 6-position of a monosaccharide (e.g., galactose, N-acetylgalactosamine, glucose, N-acetylglucosamine or mannose) which may be used as a constituting member of complex carbohydrates and has a hydroxyl group on the carbon at the 6-position. As used herein, the term "β-galactoside-α2,6-sialyltransferase activity" is intended to mean the ability described above for β-galactoside-α2,6-sialyltransferase. The term "sialic acid" as used herein refers to a neuraminic acid derivative belonging to the sialic acid family. More specifically, it refers to N-acetylneuraminic acid (Neu5Ac), N-glycolylneuraminic acid (Neu5Gc), 5-deamino-5-hydroxyneuraminic acid (KDN), disialic acid (i.e., di-N-acetylneuraminic acid; Neu5Acα2,8(9)Neu5Ac) or the like.

The β-galactoside-α2,6-sialyltransferase of the present invention is a protein comprising the amino acid sequence shown in SEQ ID NO: 2. The β-galactoside-α2,6-sialyltransferase of the present invention may also be a protein comprising the amino acid sequence shown in SEQ ID NO: 4. The amino acid sequence shown in SEQ ID NO: 4 is derived from the amino acid sequence shown in SEQ ID NO: 2 by removing amino acids 1-15 and adding methionine at the N-terminus. As described later in Example 2, a protein comprising the amino acid sequence shown in SEQ ID NO: 4 also retained the same β-galactoside-α2,6-sialyltransferase activity as a protein comprising the amino acid sequence shown in SEQ ID NO: 2. This means that the presence of at least amino acids 16-497 of SEQ ID NO: 2 allows retention of β-galactoside-α2,6-sialyltransferase activity. For this reason, the novel β-galactoside-α2,6-sialyltransferase of the present invention may be a protein comprising an amino acid sequence lacking all or part of amino acids 1-15 from amino acids 1-497 of SEQ ID NO: 2, or a protein comprising an amino acid sequence covering amino acids 16-497 of SEQ ID NO: 2.

Alternatively, the β-galactoside-α2,6-sialyltransferase of the present invention is a protein encoded by a nucleic acid comprising the nucleotide sequence shown in SEQ ID NO: 1. The β-galactoside-α2,6-sialyltransferase of the present invention may also be a protein encoded by a nucleic acid comprising the nucleotide sequence shown in SEQ ID NO: 3. The nucleotide sequence shown in SEQ ID NO: 3 corresponds to a sequence having an initiation codon (ATG) at the 5'-terminus of a nucleotide sequence covering nucleotides 46-1494 of SEQ ID NO: 1. The nucleotide sequences shown in SEQ ID NO: 1 and SEQ ID NO: 3 encode the amino acid sequences of SEQ ID NO: 2 and SEQ ID NO: 4, respectively. Alternatively, the β-galactoside-α2,6-sialyltransferase of the present invention may be a protein encoded by a nucleic acid comprising a nucleotide sequence covering nucleotides 46-1494 of SEQ ID NO: 1.

The present invention also encompasses mutants of the above β-galactoside-α2,6-sialyltransferases of the present invention, i.e., mutated proteins having β-galactoside-α2,6-sialyltransferase activity. Such mutated proteins also fall within the scope of the β-galactoside-α2,6-sialyltransferase of the present invention.

The mutant protein of the present invention may be a protein having β-galactoside-α2,6-sialyltransferase activity, which comprises an amino acid sequence comprising deletion, substitution, insertion and/or addition of one or more, or alternatively, one or several amino acids in an amino acid sequence selected from the group consisting of SEQ ID NO: 2 and SEQ ID NO: 4. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Mutants derived by amino acid deletion, substitution, insertion and/or addition can be prepared when DNAs encoding their wild-type proteins are subjected to, for example, well-known site-directed mutagenesis (see, e.g., Nucleic Acid Research, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen, and those in which a gene is selectively cleaved to remove, substitute, insert or add a selected nucleotide or nucleotides, and then ligated.

The mutant protein of the present invention may also be a protein having β-galactoside-α2,6-sialyltransferase activity, which is encoded by a nucleic acid comprising a nucleotide sequence comprising deletion, substitution, insertion and/or addition of one or more, or alternatively, one or several nucleotides in a nucleotide sequence selected from the group consisting of SEQ ID NO: 1 and SEQ ID NO: 3. Nucleotide deletion, substitution, insertion and/or addition may be accomplished by site-directed mutagenesis or other techniques as mentioned above.

The mutant protein of the present invention may further be a protein having β-galactoside-α2,6-sialyltransferase activity, which comprises an amino acid sequence sharing an amino acid identity of at least 60% or more, preferably 65% or more, 70% or more, 75% or more, 80% or more, 85% or more, 90% or more, 95% or more, 97% or more, 98% or more, or 99% or more, and more preferably 99.5% or more with an amino acid sequence selected from the group consisting of SEQ ID NO: 2 and SEQ ID NO: 4.

Alternatively, the mutant protein of the present invention may be a protein having β-galactoside-α2,6-sialyltransferase activity, which is encoded by a nucleic acid sharing an identity of at least 70% or more, preferably 75% or more, 80% or more, 85% or more, 90% or more, 95% or more, 97% or more, 98% or more, or 99% or more, and more preferably 99.5% or more with a nucleotide sequence selected from the group consisting of SEQ ID NO: 1 and SEQ ID NO: 3.

The percent identity between two amino acid sequences may be determined by visual inspection and mathematical calculation. Alternatively, the percent identity of two protein sequences may be determined by comparing sequence information based on the algorithm of Needleman, S. B. and Wunsch, C. D. (J. Mol. Biol., 48:443-453, 1970) and using the GAP computer program available from the University of Wisconsin Genetics Computer Group (UWGCG). The preferred default parameters for the GAP program include: (1) a scoring matrix, blosum62, as described by Henikoff, S, and Henikoff, J. G. (Proc. Natl. Acad. Sci. USA, 89:10915-10919, 1992); (2) a gap weight of 12; (3) a gap length weight of 4; and (4) no penalty for end gaps.

Other programs used by those skilled in the art of sequence comparison may also be used. The percent identity can be determined by comparing sequence information using, e.g., the BLAST program described by Altschul et al. (Nucl. Acids. Res., 25, p. 3389-3402, 1997). This program is available on the Internet at the web site of the National Center for Biotechnology Information (NCBI) or the DNA Data Bank of Japan (DDBJ). The details of various conditions (parameters) for identity search using the BLAST program are shown on these web sites, and default values are commonly used for search although part of the settings may be changed as appropriate. Alternatively, the percent identity of two amino acid sequences may be determined by using a program such as genetic information processing software GENETYX Ver. 7 (Genetyx Corporation, Japan) or using an algorithm such as FASTA. In this case, default values may be used for search.

The percent identity between two nucleic acid sequences can be determined by visual inspection and mathematical calculation, or more preferably, the comparison is done by comparing sequence information using a computer program. An exemplary, preferred computer program is the Genetic Computer Group (GCG; Madison, Wis.) Wisconsin package version 10.0 program, "GAP" (Devereux et al., 1984, Nucl. Acids Res., 12:387). In addition to making a comparison between two nucleic acid sequences, this "GAP" program can be used for comparison between two amino acid sequences and between a nucleic acid sequence and an amino acid sequence. The preferred default parameters for the "GAP" program include: (1) the GCG implementation of a unary comparison matrix (containing a value of 1 for identities and 0 for non-identities) for nucleotides, and the weighted amino acid comparison matrix of Gribskov and Burgess, Nucl. Acids Res., 14:6745, 1986, as described by Schwartz and Dayhoff, eds., "Atlas of Polypeptide Sequence and Structure," National Biomedical Research Foundation, pp. 353-358, 1979, or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.2.7, available for use via the National Library of Medicine website: http://www.ncbi.nlm.nih.gov/blast/bl2seq/bls.html, or the UW-BLAST 2.0 algorithm. Standard default parameter settings for UW-BLAST 2.0 are described at the following Internet site: http://blast.wustl.edu. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 544-71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The mutant protein of the present invention may also be a protein having β-galactoside-α2,6-sialyltransferase activity, which is encoded by a nucleic acid comprising a nucleotide sequence hybridizable under stringent conditions with the complementary strand of a nucleotide sequence selected from the group consisting of SEQ ID NO: 1 and SEQ ID NO: 3.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SCC to 0.2×

SSC, preferably 6×SCC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) blocking reagent and 0.5 M NaCl, and washing twice in 0.4% SDS, 0.5×SSC at 55° C. for 20 minutes and once in 2×SSC at room temperature for minutes.

Sialyltransferase activity may be measured by known procedures, e.g., those described in J. Biochem., 120, 104-110 (1996) (which is hereby incorporated by reference in its entirety). For example, the enzyme activity can be evaluated by effecting an enzymatic reaction using CMP-NeuAc (N-acetylneuraminic acid) as a glycosyl donor substrate and lactose as a glycosyl acceptor substrate, followed by evaluating the amount of the reaction product sialyllactose. It should be noted that one enzyme unit (1 U) is defined as the amount of enzyme required to transfer 1 micromole of sialic acid per minute.

Determination of the binding mode of sialic acid transferred to a glycosyl acceptor substrate may be accomplished by using, but not limited to, any procedure known to those skilled in the art, such as those using a pyridylaminated sugar chain, or reaction product analysis by nuclear magnetic resonance spectroscopy (NMR). Procedures using a pyridylaminated sugar chain comprise effecting an enzymatic reaction using a pyridylaminated sugar chain as a glycosyl acceptor substrate. More specifically, an enzymatic reaction is effected using pyridylaminated lactose (Galβ1-4Glc-PA, Takara Bio Inc., Japan) as a glycosyl acceptor substrate and CMP-NeuAc as a glycosyl donor substrate, and the reaction product is subjected to high performance liquid chromatography (HPLC) analysis. From the retention time of the reaction product, the position at which sialic acid was transferred is identified.

In an embodiment of the present invention, the enzyme of the present invention is derived from microorganisms belonging to the genus *Photobacterium*. The enzyme of the present invention is not limited in any way as long as it is derived from microorganisms belonging to the genus *Photobacterium*. It may be an enzyme derived from a new species of microorganism belonging to the genus *Photobacterium*. In a preferred embodiment, the enzyme of the present invention is derived from a microorganism belonging to *Photobacterium leiognathi*.

As to enzymological properties as well as physical and chemical properties, the β-galactoside-α2,6-sialyltransferase of the present invention is not only characterized by having β-galactoside-α2,6-sialyltransferase activity as defined above, but also has additional properties including, but not limited to, an optimum pH ranging from pH 7 to pH 9.5, preferably pH 7.5 to pH 9.5, pH 7.5 to pH 9, or pH 8 to pH 9, and more preferably pH 8. The β-galactoside-α2,6-sialyltransferase of the present invention may also be characterized by having an optimum temperature of 25° C. to 35° C. and/or a molecular weight of about 50,000±5,000 Da, as measured by SDS-PAGE analysis.

Moreover, the β-galactoside-α2,6-sialyltransferase of the present invention shows higher enzyme activity when used in a reaction solution containing phosphate buffer, as compared to other buffers such as acetate buffer, cacodylate buffer, Bis-Tris buffer, Tris-HCl buffer, TAPS buffer, CHES buffer, CAPS buffer and so on. Thus, the present invention also provides use of the β-galactoside-α2,6-sialyltransferase of the present invention, wherein the β-galactoside-α2,6-sialyltransferase is used in a reaction solution whose composition includes phosphate buffer. As used herein, the term "phosphate buffer" is interpreted to have the meaning commonly used by those skilled in the art. In a preferred embodiment, phosphate buffer is intended to mean a buffer containing phosphate ion ($PO_4^{3-}$) as a member constituting the buffering agent. In a more preferred embodiment, phosphate buffer may contain a buffering agent selected from the group consisting of sodium dihydrogen phosphate ($NaH_2PO_4$), disodium hydrogen phosphate ($Na_2HPO_4$), potassium dihydrogen phosphate ($KH_2PO_4$), dipotassium hydrogen phosphate ($K_2HPO_4$), and combinations thereof. For use in a reaction solution containing phosphate buffer, the enzyme of the present invention is preferably used at its optimum pH, i.e., within the range of pH 7 to pH 9.5.

Nucleic Acid Encoding β-galactoside-α2,6-sialyltransferase

The present invention provides a nucleic acid encoding β-galactoside-α2,6-sialyltransferase.

The nucleic acid of the present invention is a nucleic acid encoding a protein comprising an amino acid sequence selected from the group consisting of SEQ ID NO: 2 and SEQ ID NO: 4. Alternatively, the nucleic acid of the present invention is a nucleic acid comprising a nucleotide sequence selected from the group consisting of SEQ ID NO: 1 and SEQ ID NO: 3.

The nucleic acid of the present invention may be a mutant of the above nucleic acid as long as it is a nucleic acid encoding a protein having β-galactoside-α2,6-sialyltransferase activity. Such a nucleic acid also falls within the scope of the nucleic acid of the present invention encoding β-galactoside-α2,6-sialyltransferase.

Such a nucleic acid mutant is a nucleic acid encoding a protein having β-galactoside-α2,6-sialyltransferase activity, wherein the protein comprises an amino acid sequence comprising deletion, substitution, insertion and/or addition of one or more, or alternatively, one or several amino acids in an amino acid sequence selected from the group consisting of SEQ ID NO: 2 and SEQ ID NO: 4. The nucleic acid mutant of the present invention is also a nucleic acid comprising a nucleotide sequence comprising deletion, substitution, insertion and/or addition of one or more, or alternatively, one or several nucleotides in a nucleotide sequence selected from the group consisting of SEQ ID NO: 1 and SEQ ID NO: 3. Amino acid or nucleotide deletion, substitution, insertion and/or addition can be introduced as described above.

Alternatively, such a nucleic acid mutant is a nucleic acid encoding a protein having β-galactoside-α2,6-sialyltransferase activity, wherein the protein comprises an amino acid sequence sharing an identity of at least 60% or more, preferably 65% or more, 70% or more, 75% or more, 80% or more, 85% or more, 90% or more, 95% or more, 97% or more, 98% or more, or 99% or more, and more preferably 99.5% or more with an amino acid sequence selected from the group consisting of SEQ ID NO: 2 and SEQ ID NO: 4. The nucleic acid mutant of the present invention is also a nucleic acid encoding a protein having β-galactoside-α2,6-sialyltransferase activity, wherein the nucleic acid shares an identity of preferably 70% or more, 75% or more, 80% or more, 85% or more, 90% or more, 95% or more, 97% or more, 98% or more, or 99% or more, and more preferably 99.5% or more with a nucleotide sequence selected from the group consisting of SEQ ID NO: 1 and SEQ ID NO: 3. In this case, the identity between amino acid sequences or nucleotide sequences can be determined as described above.

Such a nucleic acid mutant is further a nucleic acid encoding a protein having β-galactoside-α2,6-sialyltransferase activity, wherein the nucleic acid comprises a nucleotide sequence hybridizable under stringent conditions or highly stringent conditions with the complementary strand of a nucleotide sequence selected from the group consisting of SEQ ID NO: 1 and SEQ ID NO: 3. In this case, stringent conditions or highly stringent conditions are as defined above.

Moreover, a protein encoded by the nucleic acid of the present invention is not only characterized by having β-galactoside-α2,6-sialyltransferase activity, but also has additional properties including, but not limited to, an optimum pH for its enzyme activity ranging from pH 7 to pH 9.5, preferably pH 7.5 to pH 9.5, pH 7.5 to pH 9, or pH 8 to pH 9, and more preferably pH 8. The protein encoded by the nucleic acid of the present invention may also be characterized by having an optimum temperature of 25° C. to 30° C. and/or a molecular weight of about 50,000±5,000 Da, as measured by SDS-PAGE analysis.

Microorganism Expressing β-galactoside-α2,6-sialyltransferase

The inventors of the present invention have found that microorganisms belonging to the genus *Photobacterium* of the family Vibrionaceae express a novel β-galactoside-α2,6-sialyltransferase. Thus, the present invention provides an isolated microorganism expressing the β-galactoside-α2,6-sialyl transferase of the present invention. The microorganism of the present invention is an isolated microorganism belonging to the genus *Photobacterium* and having the ability to produce the β-galactoside-α2,6-sialyltransferase of the present invention. In a preferred embodiment, the microorganism of the present invention is an isolated microorganism belonging to *Photobacterium leiognathi* and having the ability to produce the β-galactoside-α2,6-sialyltransferase of the present invention. It should be noted that the above microorganism of the genus *Photobacterium* is generally among marine bacteria, which are separated from sea water or marine products such as fish and shellfish.

The microorganism of the present invention can be separated using screening procedures as shown below, by way of example. Sea water, sea sand, sea mud or a marine product is used as a microorganism source. Sea water, sea sand and sea mud may be used directly or further diluted with sterilized sea water for use as an inoculum. In the case of small marine animals, their surface slime or the like is collected by scrubbing with a loop and is then used as an inoculum; or alternatively, their internal organs are homogenized in sterilized sea water and the resulting fluid is used as an inoculum. These inocula are applied onto agar plates such as marine broth agar 2216 medium (Becton Dickinson) or sodium chloride-supplemented nutrient agar medium (Becton Dickinson) to obtain marine microorganisms growing under various temperature conditions. After the resulting microorganisms have been pure-cultured in a routine manner, each microorganism is cultured using a liquid medium such as marine broth 2216 medium (Becton Dickinson) or sodium chloride-supplemented nutrient broth medium (Becton Dickinson). After the microorganisms are fully grown, the cells are collected by centrifugation from each culture solution. To the collected cells, 20 mM cacodylate buffer (pH 6.0) containing 0.2% Triton X-100 (Kanto Kagaku, Japan) is added, and the cells are suspended therein. This cell suspension is ultrasonicated under ice cooling to homogenize the cells. This cell homogenate is used as an enzyme solution and measured for its sialyltransferase activity in a routine manner, to thereby obtain a strain having sialyltransferase activity.

The above screening procedures were also used for obtaining *Photobacterium leiognathi* strain JT-SHIZ-145 that produces β-galactoside-α2,6-sialyltransferase characterized by having an optimum reaction pH of 7.0 to 9.5, which is described as the enzyme of the present invention.

Method for Producing Recombinant β-galactoside-α2,6-sialyltransferase

The present invention also relates to a method for producing the β-galactoside-α2,6-sialyltransferase of the present invention. In a preferred embodiment, the method of the present invention allows production of the enzyme of the present invention.

The present invention provides an expression vector carrying a nucleic acid encoding β-galactoside-α2,6-sialyltransferase, and a host cell containing the expression vector. Moreover, the present invention also provides a method for producing a recombinant β-galactoside-α2,6-sialyltransferase protein, which comprises culturing a host cell containing the expression vector under conditions suitable for recombinant protein expression, and collecting the expressed recombinant protein.

To produce the recombinant β-galactoside-α2,6-sialyltransferase protein of the present invention, an expression vector chosen depending on the host to be used is inserted with a nucleic acid sequence encoding β-galactoside-α2,6-sialyltransferase that is operably linked to a suitable transcription or translation regulatory nucleotide sequence derived from a gene of mammalian, microorganism, viral, insect or other origin. Examples of such a regulatory sequence include a transcription promoter, an operator or an enhancer, a mRNA ribosome binding site, as well as suitable sequences regulating the initiation and termination of transcription and translation.

Such a nucleic acid sequence encoding β-galactoside-α2, 6-sialyltransferase to be inserted into the vector of the present invention is a nucleotide sequence of the above nucleic acid of the present invention encoding β-galactoside-α2,6-sialyltransferase, which may or may not comprise a leader sequence. When the nucleotide sequence comprises a leader sequence, it may be a leader sequence corresponding to nucleotides 1-45 of SEQ ID NO: 1, or may be replaced by a leader sequence derived from other organisms. Leader sequence replacement enables the design of an expression system which allows secretion of the expressed protein into the extracellular environment of host cells.

Moreover, the recombinant β-galactoside-α2,6-sialyltransferase protein of the present invention may also be expressed as a fusion protein by inserting a vector with a nucleic acid designed such that a nucleic acid encoding a His tag, a FLAG™ tag, glutathione-S-transferase or the like is linked downstream of a nucleic acid encoding the enzyme. When the enzyme of the present invention is expressed as a fusion protein in this way, such a fusion protein can facilitate purification and detection of the enzyme.

Host cells suitable for protein expression of β-galactoside-α2,6-sialyltransferase include prokaryotic cells, yeast or higher eukaryotic cells. Suitable cloning and expression vectors for use in bacterial, fungal, yeast and mammalian host cells are described, for example, in Pouwels et al., Cloning Vectors: A Laboratory Manual, Elsevier, N.Y., (1985) (which is hereby incorporated by reference in its entirety).

Prokaryotic organisms include Gram-negative or Gram-positive bacteria such as *E. coli* or *Bacillus subtilis*. When a prokaryotic cell such as *E. coli* is used as a host, a β-galactoside-α2,6-sialyltransferase protein may be designed to have an N-terminal methionine residue for the purpose of facilitating recombinant polypeptide expression within prokaryotic cells. This N-terminal methionine may be cleaved from the expressed recombinant α2,6-sialyltransferase protein.

Expression vectors for use in prokaryotic host cells generally contain one or more phenotype selectable marker genes. Such a phenotype selectable marker gene is, for example, a gene imparting antibiotic resistance or auxotrophy. Examples of expression vectors suitable for prokaryotic host cells include commercially available plasmids such as pBR322 (ATCC37017) or derivatives thereof. pBR322 contains genes for ampicillin and tetracycline resistance, and thereby facilitates identification of transformed cells. DNA sequences of a suitable promoter and a nucleic acid encoding β-galactoside-α2,6-sialyltransferase are inserted into this pBR322 vector. Other commercially available vectors include, for example, pKK223-3 (Pharmacia Fine Chemicals, Uppsala, Sweden) and pGEM1 (Promega Biotech., Madison, Wis., United States).

Promoter sequences generally used in expression vectors for prokaryotic host cells include tac promoter, β-lactamase (penicillinase) promoter, and lactose promoter (Chang et al., Nature 275:615, 1978; and Goeddel et al., Nature 281:544, 1979, which are hereby incorporated by reference in their entirety).

Alternatively, a recombinant β-galactoside-α2,6-sialyltransferase protein may be expressed in yeast host cells, preferably using *Saccharomyces* (e.g., *S. cerevisiae*). Other genera of yeast, such as *Pichia* or *Kluyveromyces*, may also be used. Yeast vectors often contain an origin of replication sequence from 2μ yeast plasmid, an autonomously replicating sequence (ARS), a promoter region, sequences for polyadenylation, sequences for transcription termination, and a selectable marker gene. A yeast α-factor leader sequence can also be used to induce secretion of a recombinant β-galactoside-α2,6-sialyltransferase protein. There are also known other leader sequences that are suitable for facilitating recombinant polypeptide secretion from yeast hosts. Procedures for yeast transformation are described, for example, in Hinnen et al., Proc. Natl. Acad. Sci. USA, 75: 1929-1933, 1978 (which is hereby incorporated by reference in its entirety).

Mammalian or insect host cell culture systems can also be used to express a recombinant β-galactoside-α2,6-sialyltransferase protein. Established cell lines of mammalian origin can also be used for this purpose. Transcription and translation control sequences for mammalian host cell expression vectors may be obtained from the viral genome. Promoter and enhancer sequences commonly used are derived from polyomavirus, adenovirus 2, etc. DNA sequences derived from the SV40 viral genome (e.g., SV40 origin, early and late promoters, enhancers, splice sites, polyadenylation sites) may also be used to provide other gene elements for expression of structural gene sequences in mammalian host cells. Vectors for use in mammalian host cells can be constructed, for example, by the method of Okayama and Berg (Mol. Cell. Biol., 3: 280, 1983, which is hereby incorporated by reference in its entirety).

One method of the present invention for producing a β-galactoside-α2,6-sialyltransferase protein comprises culturing host cells transformed with an expression vector carrying a nucleic acid sequence encoding a β-galactoside-α2,6-sialyltransferase protein, under conditions allowing expression of the protein. Then, in a manner suitable for the expression system used, the β-galactoside-α2,6-sialyltransferase protein is collected from the culture medium or cell extract.

Means for purifying a recombinant β-galactoside-α2,6-sialyltransferase protein are selected, as appropriate, depending on such factors as what type of host was used and whether the protein of the present invention is to be secreted into the culture medium. For example, means for purifying a recombinant β-galactoside-α2,6-sialyltransferase protein include column chromatography on an anion exchange column, a cation exchange column, a gel filtration column, a hydroxyapatite column, a CDP-hexanolamine agarose column, a CMP-hexanolamine agarose column and/or a hydrophobic column, as well as Native-PAGE or combinations thereof. Alternatively, when a recombinant β-galactoside-α2,6-sialyltransferase is expressed in a form fused with a tag or the like for easy purification, affinity chromatographic techniques may be used for purification. For example, when a histidine tag, a FLAG™ tag or glutathione-S-transferase (GST) is fused, purification can be accomplished by affinity chromatography using a Ni-NTA (nitrilotriacetic acid) column, an anti-FLAG antibody-bound column or a glutathione-bound column, respectively.

Although a recombinant β-galactoside-α2,6-sialyltransferase may be purified to give an electrophoretically single band, the β-galactoside-2,6-sialyltransferase of the present invention may be in either purified or partially purified form because it has sufficient activity even in partially purified form.

Antibody

The present invention provides an antibody against the β-galactoside-α2,6-sialyltransferase protein of the present invention. The antibody of the present invention may be prepared against the β-galactoside-α2,6-sialyltransferase protein of the present invention or a fragment thereof. A fragment of the β-galactoside-α2,6-sialyltransferase of the present invention used for this purpose is a fragment having a sequence comprising at least 6 amino acids, at least 10 amino acids, at least 20 amino acids or at least 30 amino acids of the amino acid sequence of the enzyme.

Such an antibody may be prepared by immunizing the β-galactoside-α2,6-sialyltransferase of the present invention or a fragment thereof into animals which are used for antibody preparation in the art including, but not limited to, mice, rats, rabbits, guinea pigs and goats. The antibody may be either polyclonal or monoclonal. The antibody can be prepared based on antibody preparation techniques well known to those skilled in the art.

The antibody of the present invention can be used for collecting the β-galactoside-α2,6-sialyltransferase protein of the present invention by affinity purification. The antibody of the present invention can also be used for detecting the β-galactoside-α2,6-sialyltransferase protein of the present invention in assays such as western blotting and ELISA.

Method for Enhancing β-galactoside-α2,6-sialyltransferase Activity

The present invention also relates to a method for increasing the efficiency of glycosyltransfer reaction mediated by the β-galactoside-α2,6-sialyltransferase of the present invention.

The inventors of the present invention have found that when the β-galactoside-α2,6-sialyltransferase of the present invention is used for glycosyltransfer reaction, the efficiency of this reaction is increased upon addition of a monovalent metal ion to the reaction solution.

Thus, in one embodiment, the present invention relates to a method for increasing the efficiency of glycosyltransfer reaction mediated by the β-galactoside-α2,6-sialyltransferase of the present invention, wherein the reaction is carried out in the presence of a monovalent metal ion to thereby increase the reaction efficiency when compared to the absence of the monovalent metal ion. A preferred monovalent metal ion is sodium ion, potassium ion or lithium ion, and more preferred is sodium ion or potassium ion.

In the method of the present invention, the amount of such a monovalent metal ion is 0.05 M to 2.0 M, preferably 0.05 M to 1.5 M, 0.1 M to 1.5 M, 0.05 M to 1.0 M, or 0.1 M to 1.0 M, based on the total weight of the reaction system.

The inventors of the present invention have found that when the β-galactoside-α2,6-sialyltransferase of the present invention is used for glycosyltransfer reaction, the efficiency of this reaction is increased upon addition of calcium ion to the reaction solution.

Thus, in one embodiment, the present invention relates to a method for increasing the efficiency of glycosyltransfer reaction mediated by the β-galactoside-α2,6-sialyltransferase of the present invention, wherein the reaction is carried out in the presence of calcium ion to thereby increase the reaction efficiency when compared to the absence of calcium ion.

In the method of the present invention, the amount of calcium ion is 1.0 mM to 2.0 M, preferably 1.0 mM to 1.0 M, 1.0 mM to 500 mM, 1.0 mM to 100 mM, 5.0 mM to 2.0 M, 5.0 mM to 1.0 M, 5.0 mM to 500 mM, 5.0 mM to 100 mM, 5.0 mM to 50 mM, 5.0 mM to 25 mM, 5.0 mM to 20 mM, 10 mM to 100 mM, 10 mM to 50 mM, 10 mM to 25 mM, or 10 mM to 20 mM, based on the total weight of the reaction system.

The inventors of the present invention have also found that when the β-galactoside-α2,6-sialyltransferase of the present invention is used for glycosyltransfer reaction, the efficiency of this reaction is increased upon addition of an anion selected from the group consisting of phosphate ion, sulfate ion, nitrate ion, borate ion, chloride ion and fluoride ion to the reaction solution.

Thus, in one embodiment, the present invention relates to a method for increasing the efficiency of glycosyltransfer reaction mediated by the β-galactoside-α2,6-sialyltransferase of the present invention, wherein the reaction is carried out in the presence of an anion selected from the group consisting of a complex ion selected from the group consisting of phosphate ion, sulfate ion, nitrate ion and borate ion, as well as chloride ion, fluoride ion, and any combination thereof to thereby increase the reaction efficiency when compared to the absence of the anion. In a preferred embodiment, the anion is selected from the group consisting of a complex ion selected from the group consisting of phosphate ion, sulfate ion and nitrate ion, as well as chloride ion, and any combination thereof.

In the method of the present invention, the amount of such an anion is 0.05 M to 2.0 M, preferably 0.05 M to 1.5 M, 0.1 M to 1.5 M, 0.05 M to 1.0 M, or 0.1 M to 1.0 M, based on the total weight of the reaction system.

In another embodiment, the present invention relates to a method for increasing the efficiency of glycosyltransfer reaction mediated by the β-galactoside-α2,6-sialyltransferase of the present invention, wherein the reaction is carried out in the presence of a salt formed between a monovalent metal ion or calcium ion and an anion selected from the group consisting of a complex ion selected from the group consisting of phosphate ion, sulfate ion and nitrate ion as well as chloride ion to thereby increase the reaction efficiency when compared to the absence of the salt.

In the method of the present invention, conditions for the enzymatic reaction are not limited in any way as long as they allow the sialyltransferase of the present invention to react. For the enzymatic reaction solution, any buffer may be used including, but not limited to, cacodylate buffer, phosphate buffer, Tris-HCl buffer, Bis-Tris buffer, TAPS buffer, CHES buffer, CAPS buffer or the like. The reaction solution may be set at any pH which allows the sialyltransferase of the present invention to react, more preferably at pH 7 to 9.5, and even more preferably at an optimum pH for the sialyltransferase of the present invention. Likewise, the reaction solution may be set at any reaction temperature which allows the sialyltransferase of the present invention to react, preferably at an optimum temperature for the sialyltransferase of the present invention. Conditions for glycosyl donor and glycosyl acceptor concentrations are not limited in any way as long as they allow glycosyltransferase to react, and those skilled in the art will be able to determine these concentrations as appropriate.

In the method of the present invention, the timing of adding a monovalent metal ion, calcium ion, an anion and/or a salt to the reaction system for glycosyltransferase is not limited in any way. For example, such an ion or salt may be dissolved in an enzymatic reaction buffer, an enzyme solution, a glycosyl acceptor substrate solution or a glycosyl donor solution before use in the enzymatic reaction, or alternatively, independently of these solutions, another solution may be prepared to contain a monovalent metal ion, calcium ion, an anion and/or a salt at an appropriate concentration and added to the reaction system. In such an embodiment where a solution of a monovalent metal ion, calcium ion, an anion and/or a salt is prepared independently of enzymatic reaction components, the monovalent metal ion, calcium ion, anion and/or salt may be added to the reaction system either immediately before or during the reaction.

As used therein, the phrase "in the presence of" a monovalent metal ion, calcium ion, an anion and/or a salt is intended to mean a state where the monovalent metal ion, calcium ion, anion and/or salt is added to a reaction solution independently of a buffering agent(s) in the reaction solution.

In the method of the present invention, enhancing enzyme activity or increasing reaction efficiency is intended to mean that the efficiency of reaction is increased by carrying out the reaction in the presence of a monovalent metal ion, calcium ion, an anion and/or a salt when compared to their absence. In a preferred embodiment, enhancing enzyme activity or increasing reaction efficiency is intended to mean that when the reaction is carried out in the presence of a monovalent metal ion, calcium ion, an anion and/or a salt, the relative enzyme activity is greater than 1-fold, more preferably greater than 1.1-fold, and even more preferably greater than 1.2-fold as compared to the absence of such an ion or salt. The upper limit of increased enzyme activity may not be determined or may preferably be set to 10-fold or less, 5-fold or less, 3-fold or less, or 2-fold or less.

Advantages of the Invention

By providing a novel β-galactoside-α2,6-sialyltransferase and a nucleic acid encoding the same, the present invention makes a contribution in terms of providing a means for synthesizing and producing sugar chains, which are shown to have important functions in the body. In particular, the β-galactoside-α2,6-sialyltransferase of the present invention is characterized by having an optimum reaction pH in a neutral to alkaline range and further has a wider range of acceptor substrate specificity, when compared to conventional sialyltransferases. Sialic acid is often located at the nonreducing termini of complex carbohydrate sugar chains in the body and is a very important sugar in terms of sugar chain functions. Thus, sialyltransferase is one of the most in demand enzymes among glycosyltransferases, and the provision of the novel sialyltransferase of the present invention meets such a high demand.

BRIEF DESCRIPTION OF THE DRAWINGS

FIG. 1-2 shows the results of HPLC analysis obtained when a crude enzyme solution prepared from cultured cells of *E. coli* transformed with an expression vector carrying the β-galactoside-α2,6-sialyltransferase gene (SEQ ID NO: 3) derived from *Photobacterium leiognathi* strain JT-SHIZ-145 was mixed with pyridylaminated (PA) lactose. This figure shows the results of a control experiment relative to the experiment in FIG. 1-1, in which CMP-sialic acid serving as a sialic acid donor was not mixed into the reaction solution. The peak at a retention time of 3.962 minutes represents PA-lactose.

FIG. 1-3 shows the results of HPLC analysis obtained for a PA-lactose standard. PA-lactose appears as a peak at a retention time of 3.973 minutes.

FIG. 1-4 shows the results of HPLC analysis obtained for the reaction solution in which a known β-Galactoside-α2,6-sialyl transferase derived from *Photobacterium damselae* strain JT0160 was reacted with PA-lactose and CMP-sialic acid (i.e., pyridylaminated α2,6-sialyllactose was produced). The peaks at retention times of 3.981 and 4.470 minutes represent PA-lactose and PA-6'-sialyllactose, respectively.

FIG. 1-5 shows the results of HPLC analysis obtained for the reaction solution in which a known α2,6-sialyltransferase derived from *Photobacterium damselae* strain JT0160 was reacted with PA-lactose. This is a control experiment relative to the experiment in FIG. 1-4, in which CMP-sialic acid was not mixed into the reaction solution. The peak at a retention time of 3.976 minutes represents PA-lactose.

FIG. 2-1 is a graph showing the effect of reaction pH on the enzyme activity of recombinant β-galactoside-α2,6-sialyltransferase N1C0 (SEQ ID NO: 4) derived from *Photobacterium leiognathi* strain JT-SHIZ-145. The types of buffers used and their pH ranges are as follows: acetate buffer (pH 4-5), cacodylate buffer (pH 5-6), Bis-Tris buffer (pH 6-7), phosphate buffer (pH 6-9.5), Tris-HCl buffer (pH 7-9), TAPS buffer (pH 8-9), CHES buffer (pH 9-10), and CAPS buffer (pH 10-11).

FIG. 2-2 is a graph showing the effect of reaction temperature on the enzyme activity of recombinant β-galactoside-α2,6-sialyltransferase N1C0 derived from *Photobacterium leiognathi* strain JT-SHIZ-145.

FIG. 3 is a graph showing the effect of addition of various salts on the enzyme activity of recombinant β-galactoside-α2,6-sialyltransferase N1C0 (SEQ ID NO: 4) derived from *Photobacterium leiognathi* strain JT-SHIZ-145.

FIG. 4 is a graph showing the effect of addition of various monovalent metal ions on the enzyme activity of recombinant β-galactoside-α2,6-sialyltransferase N1C0 (SEQ ID NO: 4) derived from *Photobacterium leiognathi* strain JT-SHIZ-145.

FIG. 5 is a graph showing the effect of calcium ion addition on the enzyme activity of recombinant β-galactoside-α2,6-sialyltransferase N1C0 (SEQ ID NO: 4) derived from *Photobacterium leiognathi* strain JT-SHIZ-145.

EXAMPLES

Figure 1:
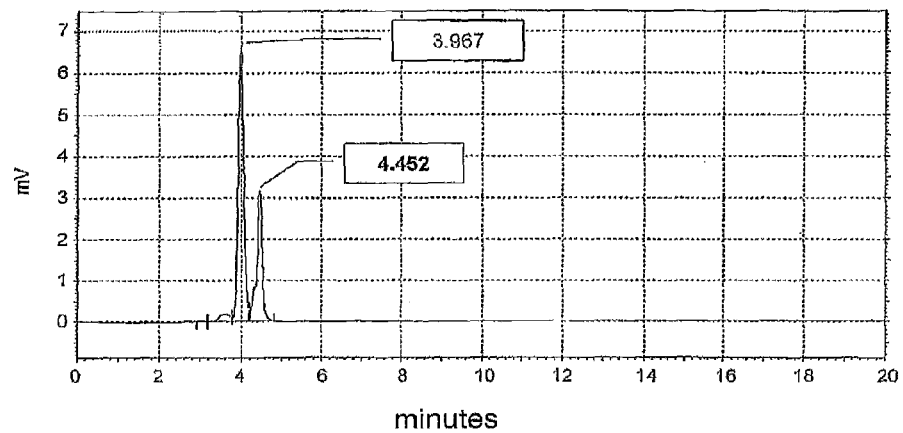
FIG. 1-1 shows the results of HPLC analysis obtained for the reaction solution in which a crude enzyme solution prepared from cultured cells of *E. coli* transformed with an expression vector carrying the β-galactoside-α2,6-sialyltransferase gene (SEQ ID NO: 3) derived from *Photobacterium leiognathi* strain JT-SHIZ-145 was reacted with pyridylaminated lactose (PA-lactose) and CMP-sialic acid. The peaks at retention times of 3.967 and 4.452 minutes represent PA-lactose and PA-6'-sialyllactose, respectively.

The present invention will now be described in more detail by way of the following examples, which are not intended to limit the technical scope of the invention. Based on the detailed description, modifications and changes will be apparent to those skilled in the art, and such modifications and changes fall within the technical scope of the invention.

Example 1

Screening and Strain Identification of Microorganisms Producing β-galactoside-α2,6-sialyltransferase (1) Screening Sea water, sea sand, sea mud or a marine product was used as an inoculum. This inoculum was applied onto agar plates containing marine broth agar 2216 medium (Becton Dickinson) to obtain microorganisms growing at 15° C., 25° C. or 30° C. After the resulting microorganisms were pure-cultured in a routine manner, each microorganism was cultured using a liquid medium composed of marine broth 2216 medium (Becton Dickinson). After the microorganisms were fully grown, the cells were collected from each culture solution by centrifugation. To the collected cells, 20 mM cacodylate buffer (pH 6.0) containing 0.2% Triton X-100 (Kanto Kagaku, Japan) was added, and the cells were suspended therein. This cell suspension was ultrasonicated under ice cooling to homogenize the cells. This cell homogenate was used as a crude enzyme solution and measured for its sialyltransferase activity, thus obtaining a strain having sialyltransferase activity, i.e., JT-SHIZ-145.

Sialyltransferase activity was measured as described in J. Biochem., 120, 104-110 (1996) (which is hereby incorporated by reference in its entirety). More specifically, the enzymatic reaction was accomplished by using CMP-NeuAc (70 nmol, containing about 20,000 cpm CMP-NeuAc in which NeuAc was labeled with $^{14}C$; NeuAc represents N-acetylneuraminic acid) as a glycosyl donor substrate, lactose (1.25 µmol) as a glycosyl acceptor substrate, NaCl added to give a concentration of 0.5 M, and the enzyme-containing reaction solution (30 µl) prepared as described above. The enzymatic reaction was carried out at 25° C. for about 10 to 180 minutes. After completion of the reaction, 1.97 ml of 5 mM phosphate buffer (pH 6.8) was added to the reaction solution, which was then applied to a Dowex 1×8 ($PO_4^{3-}$ form, 0.2×2 cm, BIO-RAD) column. Radioactivity was measured for the reaction product, i.e., sialyllactose contained in the eluate (0 to 2 ml) from this column to calculate the enzyme activity. One enzyme unit (1 U) is defined as the amount of enzyme required to transfer 1 micromole of sialic acid per minute.

To determine the binding mode of sialic acid, a reaction using PA-lactose as a substrate was then performed. The enzymatic reaction was accomplished by using the resulting crude enzyme solution and a pyridylaminated sugar chain as a glycosyl acceptor substrate. The pyridylaminated sugar chain used for analysis was pyridylaminated lactose (Galβ1-4Glc-PA, Takara Bio Inc., Japan). To 5 µl of the crude enzyme solution, 1.5 µl of 5 mM CMP-NeuAc and 1.5 µl of 10 pmol/µl glycosyl acceptor substrate were added and reacted at 25° C. for 18 hours. After completion of the reaction, the reaction solution was treated at 100° C. for 2 minutes to inactivate the enzyme, followed by HPLC to analyze the reaction product. The HPLC system used was Shimadzu LC10A (Shimadzu Corporation, Japan) and the analytical column used was Takara PALPAK Type R (Takara Bio Inc., Japan). The column which had been equilibrated with 100 mM acetate-triethylamine (pH 5.0) containing 0.15% N-butanol was injected with the reaction solution supplemented with 72 µl of Eluent A (100 mM acetate-triethylamine, pH 5.0). For elution of pyridylaminated sugar chains, Eluent A (100 mM acetate-triethylamine, pH 5.0) and Eluent B (100 mM acetate-triethylamine containing 0.5% n-butanol, pH 5.0) were used to successively elute the pyridylaminated sugar chains with a linear gradient of 30% to 50% Eluent B (0 to 20 minutes) and then 100% Eluent B (21 to 35 minutes). The analysis was performed under the following conditions: flow rate: 1 ml/min, column temperature: 40° C., detection: fluorescence (Ex: 320 nm, Em: 400 nm). As a result, the strain JT-SHIZ-145 was found to have β-galactoside-α2,6-sialyltransferase activity (FIGS. 1-1 to 1-5).

(2) Bacteriological Identification of Strain JT-SHIZ-145 by Nucleotide Sequence Analysis of 16S rRNA Gene The genomic DNA extracted from the strain JT-SHIZ-145 in a routine manner was used as a template for PCR to amplify a partial nucleotide sequence of the 16S rRNA gene, thereby determining its nucleotide sequence.

The DNA nucleotide sequence of the 16S rRNA gene in the strain JT-SHIZ-145 was found to share the highest homology (99.8%) with the sequence of the 16S rRNA gene in *Photobacterium leiognathi* the type strain ATCC25521. These results indicated that the strain JT-SHIZ-145 is a microorganism belonging to the genus *Photobacterium* of the family Vibrionaceae and is identified as belonging to *Photobacterium leiognathi*.

Example 2

Cloning and Nucleotide Sequencing of β-galactoside-α2,6-sialyltransferase Gene from Strain JT-SHIZ-145, and *E. coli* Expression of the Gene (1) Confirmation of the Presence of β-galactoside-α2,6-sialyltransferase Gene Homologue in Strain JT-SHIZ-145

To determine whether there was a homologue for the β-galactoside-α2,6-sialyltransferase gene derived from *Photobacterium damselae* strain JT0160 (Yamamoto et al. (1996) J Biochem 120: 104-110) or for the β-galactoside-α2,6-sialyltransferase gene derived from strain JT-ISH-224 (Accession No. NITE BP-87) (PCT/JP2006/304993), genomic Southern hybridization was performed on the strain JT-SHIZ-145 that was found to have β-galactoside-α2,6-sialyltransferase activity. From a cell pellet of the strain JT-SHIZ-145 (about 0.75 g), genomic DNA (about 100 µg) was prepared using a Qiagen Genomic-tip 500/G (Qiagen) in accordance with the instructions attached to the kit. The genomic DNA (several micrograms) from the strain JT-SHIZ-145 was then digested with a restriction enzyme EcoRI, HindIII, BamHI or XhoI and fractionated by 0.8% agarose gel electrophoresis, followed by alkaline blotting with 0.4 M NaOH to transfer the DNA onto a Hybond-N+ nylon membrane filter (GE Health Biosciences). Southern hybridization was performed on this filter using, as a probe, a partial fragment (i.e., an EcoRI-HindIII fragment of approximately 1.2 kb covering ATG to HindIII) of the β-galactoside-α2,6-sialyltransferase gene from *Photobacterium damselae* strain JT0160 (GeneBank Accession No. E17028) or the β-galactoside-α2,6-sialyltransferase gene from the strain JT-ISH-224 (N1C0 clone, PCT/JP2006/304993). The hybridization experiment was performed using an ECL direct labelling & detection system (GE Health Biosciences). The probe was labeled according to the instructions attached to the kit. Hybridization was accomplished at 37° C. (generally at 42° C.) for 4 hours using the hybridization buffer included in the kit, which was supplemented with 5% (w/v) blocking reagent and 0.5 M NaCl. Washing was performed twice in 0.4% SDS, 0.5×SSC at 50° C. (generally 55° C.) for 20 minutes and once in 2×SSC at room temperature for 5 minutes. Signal detection was performed according to the instructions attached to the kit. As a result, in the case of using the JT0160-derived probe, EcoRI digestion detected a band of approximately 5.5 kb, HindIII digestion detected a band of approximately 4.8 kb, and BamHI digestion detected a band of 4.8 kb. Likewise, in the case of using the JT-ISH-224-derived probe, HindIII digestion and BamHI digestion each detected a band of approximately 4.8 kb. Further, the genomic DNA of the strain JT-SHIZ-145 was also digested with a restriction enzyme PstI or HincII, and analyzed by hybridization in the same manner. As a result, in both cases of using the probes from the *Photobacterium damselae* JT0160-derived and JT-ISH-224-derived β-galactoside-α2,6-sialyl transferase genes, PstI digestion detected a band of approximately 1.6 kb, while HincII digestion detected a band of approximately 1.3 kb. These results indicated that the strain JT-SHIZ-145 had homologues for both *Photobacterium damselae* JT0160-derived and JT-ISH-224-derived β-galactoside-α2,6-sialyltransferase genes.

(2) Subcloning of Genomic Fragment Containing β-galactoside-α2,6-sialyltransferase Gene Homologue from Strain JT-SHIZ-145

In view of the foregoing, the PstI fragment of 1.6 kb appeared to contain the full length of a β-galactoside-α2,6-sialyltransferase gene homologue from the strain JT-SHIZ-145 and also appeared to be easily introduced into a plasmid vector. This fragment was inserted into plasmid vector pUC18 and provided for screening by colony hybridization.

The genomic DNA of the strain JT-SHIZ-145 was digested again with PstI, followed by agarose gel electrophoresis in TAE buffer using a low melting point agarose (SeaPlaque-GTG). A gel piece containing a DNA fragment of around 1.6 kb was excised, supplemented with an equal volume (v/w) of 200 mM NaCl and treated at 70° C. for 10 minutes to dissolved the gel. This sample was extracted once with phenol, once with phenol/chloroform, and then once with chloroform, followed by ethanol precipitation to collect a 1.6 kb DNA fragment. This fragment was ligated with a Ligation kit (Takara, Japan) to a PstI site of plasmid vector pUC18 which had been dephosphorylated. After ligation, the DNA was transformed into *E. coli* TB1 by electroporation and cultured on LA agar medium containing 100 µg/mL ampicillin and X-gal (5-bromo-4-chloro-3-indolyl-β-D-galactoside). 400 white colonies, into which the DNA fragment appeared to be inserted, were inoculated onto another LA agar medium containing the above antibiotic. The surface of each plate on which colonies were formed was contacted with a Hybond-N+ nylon membrane filter (GE Health Biosciences) to transfer the colonies onto the membrane. The colonies were then treated with alkaline according to the instructions attached to the membrane to cause DNA denaturation, and fixed on the membrane. Colony hybridization was performed on this membrane by using, as a probe, the β-galactoside-α2,6-sialyltransferase gene from the strain JT-ISH-224. As a result, signals were detected in 4 colonies. It should be noted that probe labeling and hybridization conditions were the same as in the case of using an ECL system as shown above.

These colonies were inoculated into ampicillin-containing LB liquid medium and cultured overnight with shaking at 37° C., followed by plasmid extraction in a routine manner (Sambrook et al. 1989, Molecular Cloning, A laboratory manual, 2$^{nd}$ edition (hereby incorporated by reference in its entirety)) and restriction enzyme analysis to confirm the insertion of the 1.6 kb fragment.

(3) Determination of the Entire Nucleotide Sequence of β-galactoside-α2,6-sialyltransferase Gene Homologue from Strain JT-SHIZ-145

With respect to one of the plasmids that were confirmed above to carry the insert DNA, nucleotide sequences at both ends of the 1.6 kb PstI fragment were determined by using M13 primers (Takara, Japan) in an ABI PRISM fluorescent sequencer (Model 310 Genetic Analyzer, Perkin Elmer). The resulting DNA sequences were translated into amino acid sequences using genetic information processing software GENETYX Ver. 7 (Genetyx Corporation, Japan), and an identity search with the BLAST program was made for these amino acid sequences against the GeneBank database of the National Center for Biotechnology Information (NCBI). As a result, the amino acid sequence translated from one of the DNA sequences showed significant homology with the amino acid sequence of β-galactoside-α2,6-sialyltransferase derived from *Photobacterium damselae* strain JT0160. The orientation of the region showing homology suggested that the 1.6 kb PstI fragment contained the entire β-galactoside-α2,6-sialyltransferase gene homologue from the strain JT-SHIZ-145.

Next, to determined the entire DNA sequence of this enzyme gene homologue from the strain JT-SHIZ-145, the following two primers were synthesized based on the DNA sequence obtained from the 1.6 kb PstI fragment, and used for nucleotide sequencing:

```
SHIZ145 26 N1
(5'-GCCATCATTACAGCAGTTAATG-3' (22mer):
SEQ ID NO: 5);
and

SHIZ145 26 N2
(5'-TGAGTATTCACAGAATGAGCGC-3' (22mer):
SEQ ID NO: 6).
```

Using these primers, nucleotide sequencing was performed. As a result, the sequence of SEQ ID NO: 1 in the Sequence Listing was obtained. This sequence corresponds to the entire nucleotide sequence of the open reading frame (ORF) of the β-galactoside-α2,6-sialyltransferase gene homologue from the strain JT-SHIZ-145. The ORF of the β-galactoside-α2,6-sialyltransferase gene homologue from the strain JT-SHIZ-145 was composed of 1494 base pairs and encoded 497 amino acids. This amino acid sequence is shown in SEQ ID NO: 2 in the Sequence Listing. Upon analysis of DNA and amino acid sequences using GENETYX Ver. 7, the DNA sequence of the β-galactoside-α2,6-sialyltransferase gene homologue from the strain JT-SHIZ-145 was found to share 68.2% homology with the β-galactoside-α2,6-sialyltransferase gene from *Photobacterium damselae* strain JT0160. Likewise, its amino acid sequence was found to share 66.3% homology with β-galactoside-α2,6-sialyltransferase (JC5898) from *Photobacterium damselae* strain JT0160. Moreover, this homologue was found to share 63.7% homology at the nucleotide sequence level and 55.1% homology at the amino acid sequence level with the β-galactoside-α2,6-sialyltransferase gene from the strain JT-ISH-224.

(4) Construction of Expression Vector for β-galactoside-α2,6-sialyltransferase Gene Homologue from Strain JT-SHIZ-145

To test whether the cloned gene encoded a protein having sialyltransferase activity, the full length of the gene homologue and its derivative modified to remove a region encoding the N-terminal signal peptide were each integrated into an expression vector to produce a protein in *E. coli* cells, followed by measuring the activity of this expressed protein.

Genetic information processing software GENETYX Ver. 7 was used to analyze an amino acid sequence encoding the β-galactoside-α2,6-sialyltransferase gene homologue from the strain JT-SHIZ-145, estimating that the N-terminal 15 amino acids would constitute the signal peptide. Then, a primer pair for cloning the full-length gene (herein referred to as "SHIZ145-N0C0"):

```
SHIZ145 N0 BspHI
(5'-AAAGGGTCATGAAAAGAATATTTTGTTTA-3' (29mer):
SEQ ID NO: 7);
and SHIZ145 C0 Hind
(5'-ATGAGCAAGCTTTCAGCACCAAAATAGAACATC-3' (33mer):
SEQ ID NO: 8),
``` as well as a primer pair for cloning a gene encoding a protein lacking the amino acids of the signal peptide region (herein referred to as "SHIZ145-N1C0"):

```
SHIZ145 N1 Pci
(5'-TATACATGTGTAATGATAATCAGAATACAG-3' (30mer):
SEQ ID NO: 9);
and SHIZ145 C0 Hind
(5'-ATGAGCAAGCTTTCAGCACCAAAATAGAACATC-3' (33mer):
SEQ ID NO: 8)
``` were designed and synthesized.

PCR was carried out with these primers using the plasmid carrying the 1.6 kb PstI fragment as a template to amplify the β-galactoside-α2,6-sialyltransferase gene homologue from the strain JT-SHIZ-145 for use in integration into an expression vector. The reaction conditions for PCR were set as follows. In 50 μl reaction solution containing 500 ng template DNA, 5 μl 10× PyroBest buffer II, 4 μl 2.5 mM dNTPs, 50 pmol primer and 0.5 μl PyroBest DNA Polymerase (Takara, Japan), PCR was carried out using a Program Temp Control System PC-700 (ASTEK) under the following conditions: 96° C. for 3 minutes, (96° C. for 1 minute, 55° C. for 1 minute, 72° C. for 2 minutes)×5 cycles, and 72° C. for 6 minutes. As a result, PCR products of approximately 1.5 kb and 1.45 kb were amplified for SHIZ145-N0C0 and SHIZ145-N1C0, respectively. These PCR products were each cloned into vector pCR4TOPO (Invitrogen). Ligation was carried out according to the instructions attached to the vector kit. Each DNA was introduced into *E. coli* TB1 by electroporation and the plasmid DNA was extracted in a routine manner (Sambrook et al. 1989, Molecular Cloning, A laboratory manual, 2$^{nd}$ edition). Clones confirmed to have the insert were each analyzed by PCR with M13 primers (Takara, Japan) to determine the nucleotide sequence of each PCR product from both ends using an ABI PRISM fluorescent sequencer (Model 310 Genetic Analyzer, Perkin Elmer). As a result, it was confirmed that mutation-free SHIZ145-N0C0 (SEQ ID NO: 1) and SHIZ145-N1C0 (SEQ ID NO: 3) were cloned.

Clones of SHIZ145-N0C0 and SHIZ145-N1C0 whose nucleotide sequences were confirmed were double-digested with restriction enzymes BspHI & HindIII (for SHIZ145-N0C0) or PciI & HindIII (for SHIZ145-N1C0), followed by gel purification of each DNA fragment as described above. pTrc99A (Pharmacia LKB) was used as a vector for *E. coli* expression. After being double-digested with restriction enzymes NcoI & HindIII and purified on a gel, this vector was ligated with the DNA fragment of SHIZ145-N0C0 or SHIZ145-N1C0 prepared as described above using a Ligation Kit (Takara, Japan) and transformed into *E. coli* TB1. In a routine manner, the plasmid DNA was extracted and analyzed by restriction enzyme analysis to confirm the integration of the DNA fragment into the expression vector, thereby completing SHIZ145-N0C0/pTrc99A or SHIZ145-N1C0/pTrc99A.

(5) Expression Induction and Activity Measurement

Among the two expression vectors obtained above, SHIZ145-N1C0/pTrc99A was used to perform an induction experiment of protein expression. A single colony of *E. coli* TB1 having the expression vector pTrc99A carrying the SHIZ145-N1C0 clone (SEQ ID NO: 3) was inoculated into LB medium (6 ml) containing an antibiotic, ampicillin (final concentration 100 µg/mL), and pre-cultured at 30° C. to about $A_{600}$=0.5, followed by addition of IPTG (isopropyl-β-D-(−)-thiogalactopyranoside, Wako Pure Chemical Industries, Ltd., Japan) at a final concentration of 1 mM to initiate expression induction. After culturing overnight with shaking at 30° C., the cells in 2 ml culture solution were collected by centrifugation. These cells were suspended in 400 µl of 20 mM Bis-Tris buffer (pH 6.0) containing 0.336% Triton X-100, and ultrasonically homogenized under ice cooling. The resulting homogenate was defined as a crude enzyme solution and provided for sialyltransferase activity measurement. Measurement was accomplished as described in J. Biochem., 120, 104-110 (1996) (hereby incorporated by reference in its entirety). More specifically, CMP-NeuAc as a glycosyl donor substrate (70 nmol, containing about 20,000 cpm CMP-NeuAc in which NeuAc was labeled with $^{14}$C; NeuAc represents N-acetylneuraminic acid), 0.5 M NaCl, 120 mM lactose as a glycosyl acceptor substrate, and the crude enzyme solution (5 µl) prepared as described above were mixed and reacted at 30° C. for 30 minutes, followed by addition of 5 mM phosphate buffer (pH 6.8, 1.97 ml) to stop the reaction. This solution was applied to a Dowex 1×8 ($PO_4^{3-}$ form, 0.2×2 cm, BIO-RAD) column. Radioactivity was measured for the reaction product, i.e., sialyllactose contained in the eluate from the column to calculate the enzyme activity. The measurement was performed in duplicate, and indicated that the crude enzyme solution from *E. coli* cells containing SHIZ145-N1C0 had the ability to transfer $^{14}$C-labeled NeuAc in the glycosyl donor CMP-NeuAc to the glycosyl acceptor substrate lactose, i.e., had sialyltransferase activity. More specifically, a homogenate prepared from *E. coli* cells transformed with pTrc99A vector carrying no insert (negative control) was found to have a radioactivity of 156 cpm, whereas a homogenate prepared from *E. coli* cells transformed with the expression vector pTrc99A carrying the SHIZ145-N1C0 clone was found to have a radioactivity of 8326 cpm.

In view of the foregoing, the cloned homologue was found to be a gene (SEQ ID NO: 3) encoding β-galactoside-α2,6-sialyltransferase from the strain JT-SHIZ-145 (SEQ ID NO: 4).

TABLE 1

Enzyme activity of crude enzyme solution prepared from *E. coli* cells transformed with SHIZ145-N1C0/pTrc99A

| Crude enzyme | | NeuAc transferred (cpm) |
|---|---|---|
| Insert | − | 156 |
| Insert | + | 8326 |

(6) Confirmation of β-galactoside-α2,6-sialyltransferase Activity

Further analysis was performed to examine whether sialyltransferase expressed by *E. coli* cells transformed in (5) above with SHIZ145-N1C0/pTrc99A had β-galactoside-α2,6-sialyltransferase activity. As in the case of Example 1, pyridylaminated lactose (Galβ1-4Glc-PA, PA-Sugar Chain 026, Takara Bio Inc., Japan) was used as a glycosyl acceptor to carry out the enzymatic reaction. As a result, PA-6'-sialyllactose (Neu5Acα2-6Galβ1-4Glc-PA) was detected, as in the case of Example 1. These results demonstrated that the β-galactoside-α2,6-sialyltransferase gene from *Photobacterium* sp. strain JT-SHIZ-145 was cloned and expressed in *E. coli* cells.

Example 3

Extraction and Purification of β-galactoside-α2,6-sialyltransferase from *E. coli* TB1 Having Expression Vector pTrc99A Carrying SHIZ145-N1C0 Clone From colonies of *E. coli* TB1 having the expression vector pTrc99A carrying the SHIZ145-N1C0 clone (SEQ ID NO: 3) which had been subcultured on LBAmp agar plates, the cells were collected with a loop, inoculated into 6 ml-LB liquid medium supplemented with 30 µl of ×200 ampicillin (400 mg/20 ml), and cultured with shaking at 30° C. at 180 rpm for 8 hours.

Main culturing was accomplished in the following manner. 300 ml-LB medium supplemented with 1.5 ml of ×200 ampicillin (400 mg/20 ml) and 300 µl of 1 M IPTG (1.192 g/5 ml) was charged into a 1000 ml baffle flask. The same medium was prepared in 9 flasks (2.7 L in total). Each flask was inoculated with the above culture solution (12 ml) and cultured with shaking at 30° C. at 180 rpm for 24 hours. The cultured medium was centrifuged to collect the cells.

The cells were suspended in 990 ml of 20 mM Bis-Tris buffer (pH 7.0) containing 0.336% Triton X-100 to give a concentration of 1.6 g/26 ml, and ultrasonically homogenized under ice cooling. The cell homogenate was centrifuged at 4° C. at 100,000×g for 1 hour to obtain the supernatant.

This crude enzyme solution was loaded to a HiLoad 26/10 Q Sepharose HP (Amersham) anion exchange column, which had been equilibrated with 20 mM Bis-Tris buffer (pH 7.0) containing 0.336% Triton X-100. The column was eluted with a linear gradient up to 1 M sodium chloride in 20 mM Bis-Tris buffer (pH 7.0) containing 0.336% Triton X-100 to thereby collect an enzymatically active fraction eluted at around 0.25 M sodium chloride concentration.

The collected fraction was diluted with 20 mM phosphate buffer (pH 7.0) and loaded to hydroxyapatite (Bio-Rad) which had been equilibrated with 20 mM phosphate buffer (pH 7.0) containing 0.336% Triton X-100, followed by elution with a linear gradient from 20 mM phosphate buffer (pH 7.0) containing 0.336% Triton X-100 to 500 mM phosphate buffer (pH 7.0) containing 0.336% Triton X-100 to thereby collect an enzymatically active fraction eluted at around 125 mM phosphate buffer concentration.

This enzymatically active fraction was then gel-filtered by being applied to a gel filtration column Superdex (Amersham), which had been equilibrated with 20 mM Bis-Tris buffer (pH 7.0) containing 0.2 M sodium chloride and 0.336% Triton X-100, to thereby collect a protein fraction having sialyltransferase activity.

This enzymatically active fraction was then loaded again to a MonoQ 5/50 GL (Amersham) anion exchange column. The column was eluted with a linear gradient up to 1 M sodium chloride in 20 mM Bis-Tris buffer (pH 7.0) containing 0.336% Triton X-100 to thereby collect an enzymatically active fraction.

The enzymatically active fraction was electrophoresed on an SDS-polyacrylamide gel (the concentration of the acrylamide gel: 12.5%), indicating that the target enzyme showed a single band with a molecular weight of about 50,000.

As to purification of β-galactoside-α2,6-sialyltransferase of the SHIZ145-N1C0 clone from a crude enzyme solution, Table 2 shows the enzyme activity of the sample after each of the purification steps mentioned above. The enzyme activity was measured by the method reported in J. Biochem. 120, 104-110 (1996), as in the case of Example 1. For protein quantification, a Coomassie Protein Assay Reagent (PIERCE) was used according to the instruction manual attached thereto. One enzyme unit (1 U) was defined as the amount of enzyme required to transfer 1 micromole of sialic acid per minute.

(SEQ ID NO: 4) was found to have an optimum pH in the range of pH 7.0 to 9.5. Moreover, particularly high activity was observed in phosphate buffer, and the enzyme activity reached maximum at pH 8.0. It should be noted that enzyme activity at each pH was evaluated as relative activity, assuming that the enzyme activity at pH 8.0 in phosphate buffer was set to 1.

(2) Optimum Temperature for Enzyme Activity of JT-SHIZ-145-Derived Recombinant β-galactoside-α2,6-sialyltransferase N1C0

The enzyme activity was measured at an interval of 5° C. starting from 10° C. up to 50° C. using phosphate buffer (pH 8.0).

Figures 1, 2:
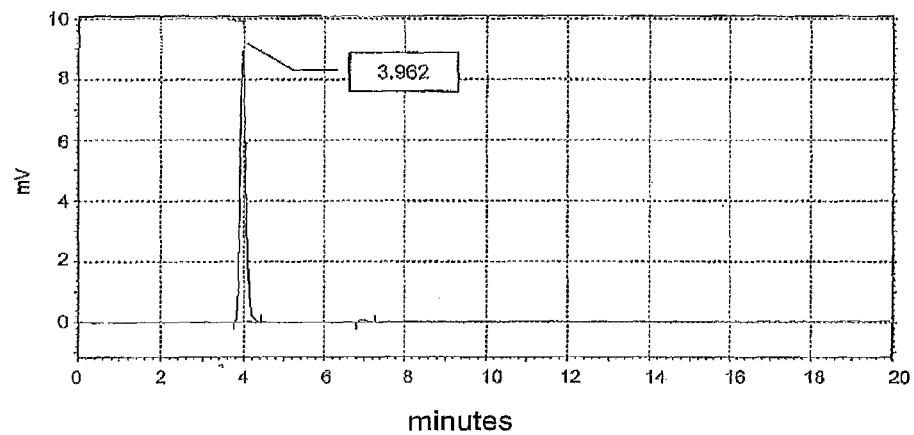

As a result, as shown in FIG. 2-2, the enzyme activity was maximum at 30° C. It should be noted that enzyme activity at each temperature was evaluated as relative activity, assuming that the enzyme activity at 30° C. was set to 100.

Example 5

Glycosyl Acceptor Substrate Specificity of JT-SHIZ-145-Derived Recombinant β-galactoside-α2,6-sialyltransferase N1C0 (SEQ ID NO: 4)

The purified enzyme prepared in Example 3 for JT-SHIZ-145-derived recombinant β-galactoside-α2,6-sialyltransferase N1C0 (SEQ ID NO: 4) was used to cause sialic acid transfer reaction in various monosaccharides/disaccharides

TABLE 2

Purification of recombinant β-galactoside-α2,6-sialyltransferase N1C0 from *E. coli* cells transformed with SHIZ145-N1C0/pTrc99A

| Sample | Volume (ml) | Unit/ml | Total protein | Total activity | Specific activity | Yield (%) | Purification degree (fold) |
|---|---|---|---|---|---|---|---|
| Crude enzyme solution | 360 | 0.14 | 750.46 | 52.1 | 0.07 | 100.00 | 1.000 |
| Q sepharose | 29.5 | 4.40 | 238.04 | 129.8 | 0.55 | 248.89 | 7.847 |
| HAP | 3.6 | 21.41 | 47.71 | 77.1 | 1.62 | 147.83 | 23.256 |
| Superdex | 5 | 1.01 | 3.88 | 5.1 | 1.31 | 9.71 | 18.761 |
| Mono Q | 3.5 | 1.27 | 2.43 | 4.4 | 1.82 | 8.51 | 26.264 |

Example 4

Optimum pH and Optimum Temperature for Enzyme Activity of Recombinant β-galactoside-α2,6-sialyltransferase N1C0 (SEQ ID NO: 4) Derived from Strain JT-SHIZ-145

The purified enzyme prepared in Example 3 was used to examine the optimum pH and optimum temperature for JT-SHIZ-145-derived recombinant β-galactoside-α2,6-sialyltransferase N1C0 (SEQ ID NO: 4).

(1) Optimum pH for Enzyme Activity of JT-SHIZ-145-Derived Recombinant β-galactoside-α2,6-sialyltransferase N1C0

Acetate buffer (pH 4-5), cacodylate buffer (pH 5-6), Bis-Tris buffer (pH 6-7), phosphate buffer (pH 6-9.5), Tris-HCl buffer (pH 7-9.5), TAPS buffer (pH 8-9), CHES buffer (pH 9-10) and CAPS buffer (pH 10-11) were prepared and used for enzyme activity measurement at 30° C. at various pH values.

As a result, as shown in FIG. 2-1, JT-SHIZ-145-derived recombinant β-galactoside-α2,6-sialyltransferase N1C0 as glycosyl acceptor substrates. The reaction was accomplished as described in J. Biochem., 120, 104-110 (1996).

The monosaccharides used as glycosyl acceptor substrates were the following 8 types: methyl-α-D-galactopyranoside (Gal-α-OMe), methyl-β-D-galactopyranoside (Gal-β-OMe), methyl-α-D-glucopyranoside (Glc-α-OMe), methyl-β-D-glucopyranoside (Glc-β-OMe), methyl-α-D-mannopyranoside (Man-α-OMe), methyl-β-D-mannopyranoside (Man-β-OMe), N-acetylgalactosamine (GalNAc), and N-acetylglucosamine (GlcNAc). The disaccharides used were the following 3 types: lactose (Gal-β1,4-Glc), N-acetyllactosamine (Gal-β1,4-GlcNAc) and Gal-β1,3-GalNAc.

As a result, sialic acid was found to be efficiently transferred to methyl-β-D-galactopyranoside, N-acetylgalactosamine, lactose, N-acetyllactosamine and Gal-β1,3-GalNAc among the 11 types of monosaccharides and disaccharides used as glycosyl acceptor substrates in this experiment (Table 3). It should be noted that the relative activity toward each acceptor substrate was calculated assuming that the sialyltransferase activity toward lactose was set to 100.

TABLE 3

Transfer of sialic acid to monosaccharides and disaccharides by recombinant β-galactoside-α2,6-sialyltransferase N1C0 purified from *E. coli* cells transformed with SHIZ145-N1C0/pTrc99A

| Glycosyl acceptor substrate | % (nmol) |
|---|---|
| Gal-α-OMe | 2% |
| Gal-β-OMe | 59% |
| Glc-α-OMe | 0% |
| Glc-β-OMe | 0% |
| Man-α-OMe | 0% |
| Man-β-OMe | 0% |
| GalNAc | 35% |
| GlcNAc | 6% |
| Gal-β1,4-GlcNAc | 205% |
| Gal-β1,4-Glc | 100% |
| Gal-β1,3-GalNAc | 71% |

Example 6

Comparison of Acceptor Substrate Specificity Toward Glycoproteins in JT-SHIZ-145-Derived Recombinant β-galactoside-α2,6-sialyltransferase N1C0 (SEQ ID NO: 4)

As a glycosyl acceptor substrate, asialofetuin and asialomucin were each used. Asialofetuin or asialomucin (2 mg) was dissolved in 1 ml of 20 mM Bis-Tris buffer (pH 7.0) and used as a glycosyl acceptor substrate solution. As a glycosyl donor substrate, CMP-NeuAc was used. The glycosyl acceptor substrate solution (40 μl), the glycosyl donor substrate (5 μl) and the enzyme solution (5 μl) were mixed and incubated at 30° C. for 0.5 hours to cause sialic acid transfer reaction. After completion of the reaction, the reaction solution was gel-filtered by being applied to a Sephadex G-50 Superfine (0.8×18.0 cm) equilibrated with 0.1 M sodium chloride. A glycoprotein-containing eluate fraction (2-4 ml fraction) from gel filtration was collected and measured for its radioactivity using a liquid scintillation counter to quantify sialic acid transferred to the glycosyl acceptor substrate.

As a result, sialic acid was found to be transferred to both glycosyl acceptor substrates.

TABLE 4

Transfer of sialic acid to glycoproteins by recombinant β-galactoside-α2,6-sialyltransferase N1C0 purified from *E. coli* cells transformed with SHIZ145-N1C0/pTrc99A

| Acceptor | | NeuAc transferred (cpm) |
|---|---|---|
| Asialomucin | − | 210 |
| Asialomucin | + | 9060 |
| Asialomucin | + | 10204 |
| Asialofetuin | − | 56 |
| Asialofetuin | + | 2140 |
| Asialofetuin | + | 2038 |

Example 7

Effect of Various Ions on Enzyme Activity of JT-SHIZ-145-Derived Recombinant β-galactoside-α2,6-sialyltransferase N1C0 (SEQ ID NO: 4)

(1) Effect of Complex Ions on Enzyme Activity of JT-SHIZ-145-Derived Recombinant β-galactoside-α2,6-sialyltransferase N1C0

Aqueous solutions were prepared for potassium nitrate ($KNO_3$), sodium nitrate ($NaNO_3$), potassium sulfate ($K_2SO_4$), sodium sulfate ($Na_2SO_4$), sodium dihydrogen phosphate ($NaH_2PO_4$), disodium hydrogen phosphate ($Na_2HPO_4$) and potassium phosphate ($KH_2PO_4+K_2HPO_4$ (abbreviated as KPB)). These aqueous solutions were each adjusted with Tris-HCl buffer to give an anion concentration of 0.1 M in the reaction solution at 30° C., and used for enzyme activity measurement.

Figures 1, 2, 3:
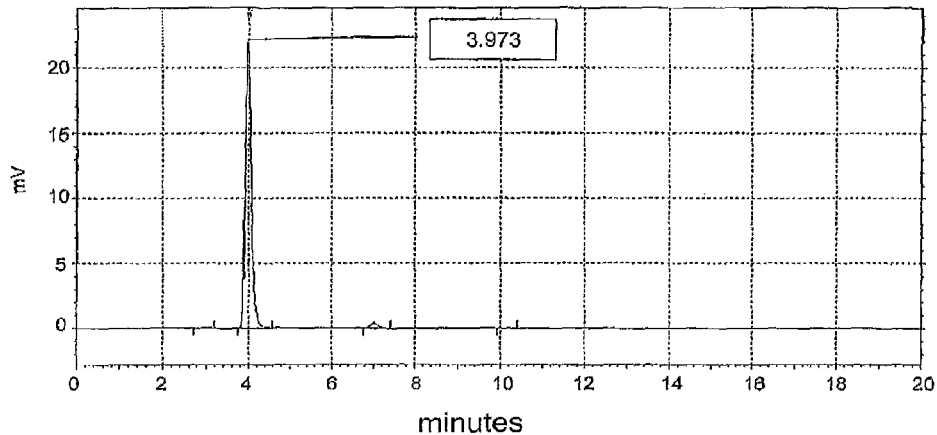

As a result, as shown in FIG. 3, the enzyme activity was maximum upon addition of potassium phosphate (KPB) or disodium hydrogen phosphate. Moreover, not only upon addition of phosphate ion, but also upon addition of a salt containing another complex ion such as sulfate ion or nitrate ion, the enzyme activity was also significantly increased when compared to the absence of addition. It should be noted that enzyme activity in the reaction solution upon addition of each solution was evaluated as relative activity, assuming that the enzyme activity in the absence of addition (i.e., in Tris-HCl alone) was set to 1.

(2) Effect of $Na^+$ or $K^+$ Ion on Enzyme Activity of JT-SHIZ-145-Derived Recombinant β-galactoside-α2,6-sialyltransferase N1C0

Aqueous solutions were prepared for potassium nitrate ($KNO_3$), sodium nitrate ($NaNO_3$), potassium sulfate ($K_2SO_4$), sodium sulfate ($Na_2SO_4$), sodium dihydrogen phosphate ($NaH_2PO_4$), disodium hydrogen phosphate ($Na_2HPO_4$) and potassium phosphate ($KH_2PO_4+K_2HPO_4$ (abbreviated as KPB)). These aqueous solutions were each adjusted with Tris-HCl buffer to give an anion concentration of 0.1 M in the reaction solution at 30° C., and used for enzyme activity measurement.

As a result, as shown in FIG. 3, the enzyme activity was maximum upon addition of potassium phosphate (KPB) or disodium hydrogen phosphate. Moreover, upon addition of the other aqueous solutions containing potassium/sodium, the enzyme activity was also significantly increased when compared to the absence of addition. It should be noted that enzyme activity in the reaction solution upon addition of each solution was evaluated as relative activity, assuming that the enzyme activity in the absence of addition (i.e., in Tris-HCl alone) was set to 1.

(3) Effect of $Na^+$, $K^+$ or $Li^+$ Ion on Enzyme Activity of JT-SHIZ-145-Derived Recombinant β-galactoside-α2,6-sialyltransferase N1C0

Aqueous solutions were prepared for potassium chloride (KCl), sodium chloride (NaCl) and lithium chloride (LiCl). These aqueous solutions were each adjusted with Tris-HCl buffer to give a cation concentration of 0.1 M, 0.2 M or 0.5 M in the reaction solution at 30° C., and used for enzyme activity measurement.

Figures 1, 2, 3, 4:
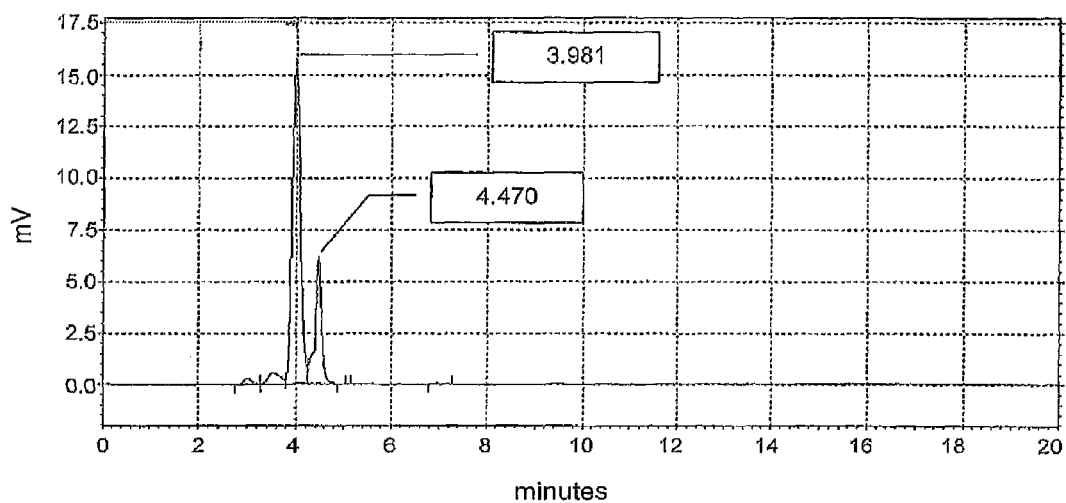

As a result, as shown in FIG. 4, the enzyme activity was significantly increased when compared to the absence of addition. It should be noted that enzyme activity in the reaction solution upon addition of each solution was evaluated as relative activity, assuming that the enzyme activity in the absence of addition (i.e., in Tris-HCl alone) was set to 1.

(4) Effect of Calcium Ion on Enzyme Activity of JT-SHIZ-145-derived Recombinant β-galactoside-α2,6-sialyltransferase N1C0

Using a crude enzyme solution, enzyme activity was measured in a reaction solution adjusted to contain calcium chloride and/or EDTA at a final concentration of 10 mM for calcium ion and 50 mM for EDTA.

Figures 1, 2, 3, 4, 5:
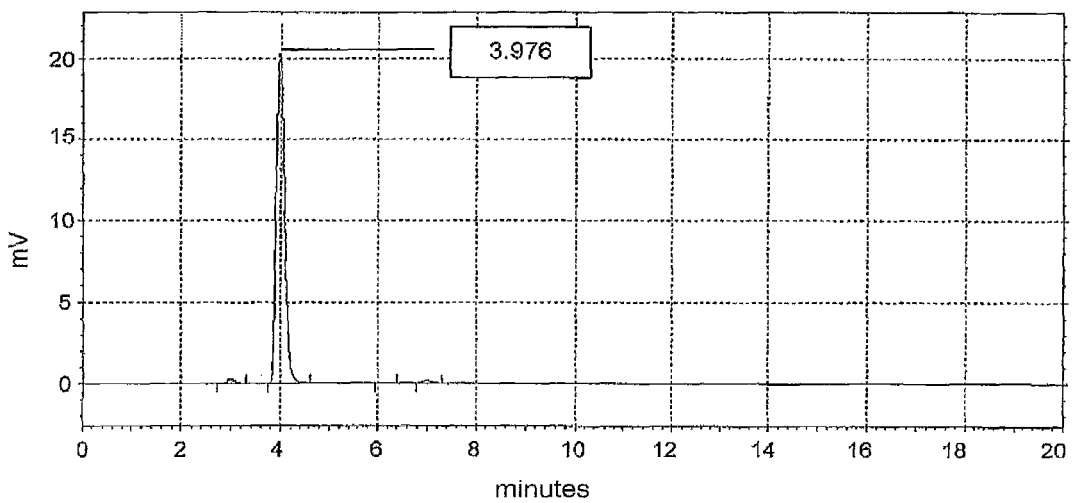
Figures 1, 2:
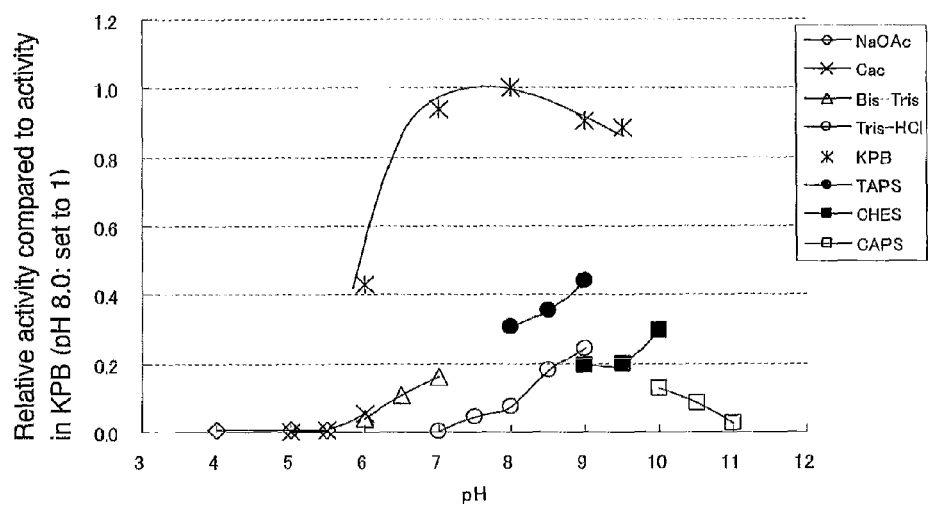
Figure 2:
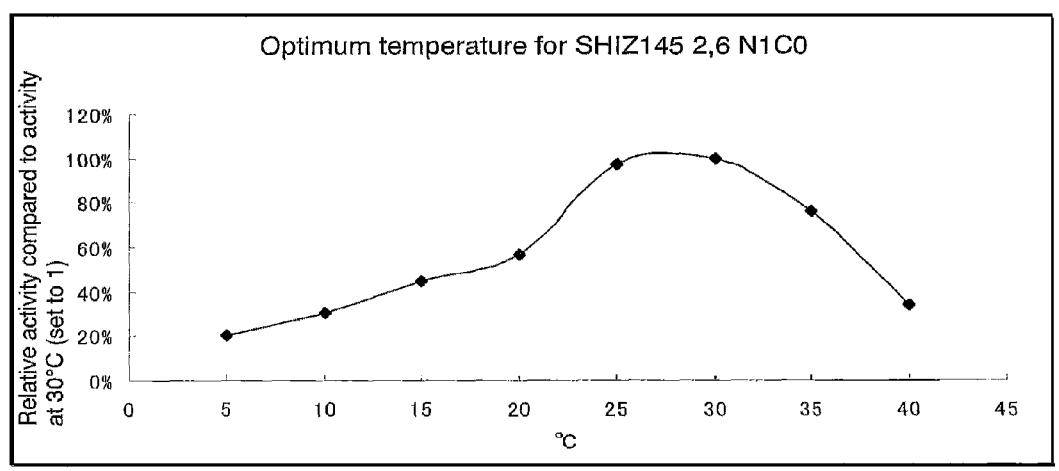
Figure 3:
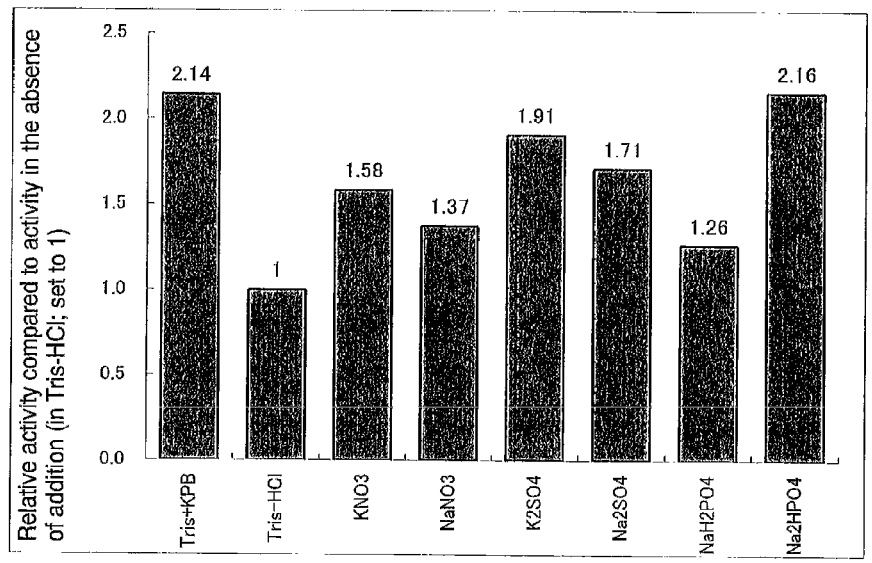
Figure 4:
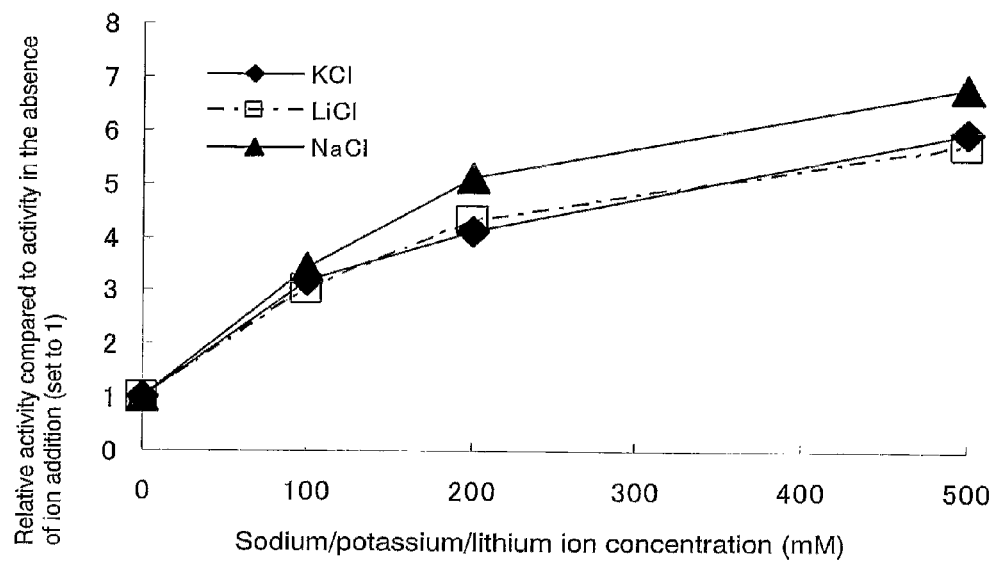
Figure 5:
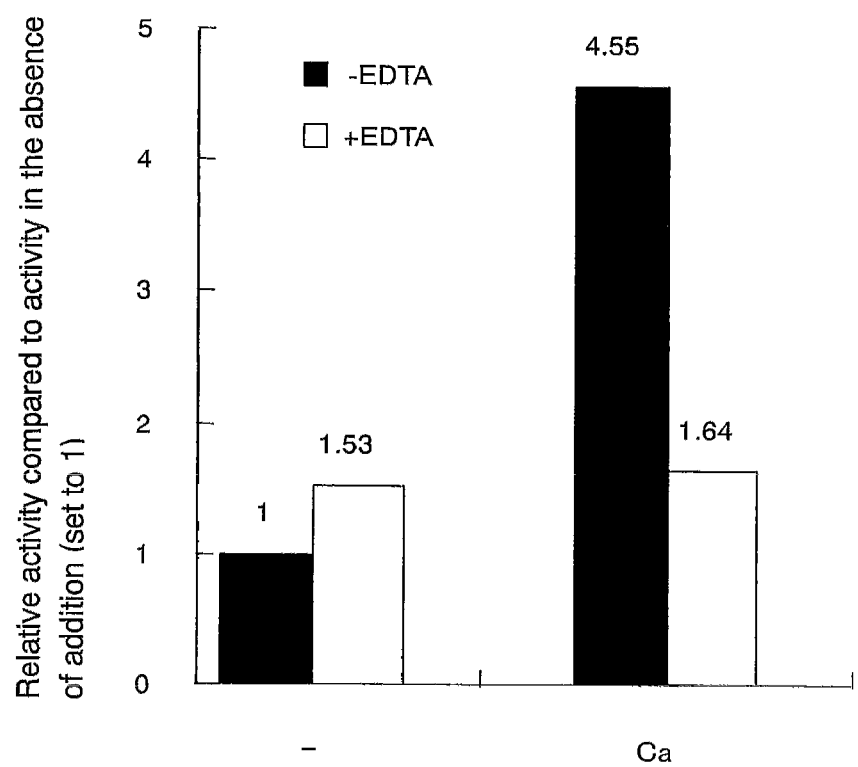

As a result, as shown in FIG. 5, the enzyme activity in the presence of calcium ion was remarkably increased when compared to the absence of calcium ion. It should be noted that when calcium ion was added to the reaction system together with a chelating agent EDTA, the enzyme activity was almost the same level as in the absence of calcium ion.

Example 8

Confirmation of Sialyltransferase Activity in Photobacterium leiognathi Strains Other than JT-SHIZ-145

*Photobacterium leiognathi* the type strain NCIMB2193 (ATCC25521), as well as *Photobacterium leiognathi* strains NCIMB1511 (ATCC25587) and NCIMB2134 (ATCC33469) were each cultured in 6 ml of sea water yeast peptone medium (3.0 g/l yeast extract and 5.0 g/l peptone), from which crude enzyme solutions were then prepared as described in Example 2-(5) above and provided for sialyltransferase activity measurement. As a result, as shown in Table 5, the radioactivity was 500 to 600 cpm both in the absence of the crude enzyme solutions (buffer alone, negative control) and in the presence of the crude enzyme solutions. This result indicates that a plurality of *Photobacterium leiognathi* strains available in the art have no sialyltransferase or have extremely weak enzyme activity that is below the detection limit. In contrast, the strain JT-SHIZ-145 has high sialyltransferase activity although it is among *Photobacterium leiognathi* strains.

TABLE 5

Sialyltransferase activity in other *Photobacterium leiognathi* strains

| Strain name | NeuAc transferred (cpm) |
|---|---|
| — | 566 |
| NCIMB2193 | 518 |
| NCIMB1511 | 541 |
| NCIMB2134 | 615 |

INDUSTRIAL APPLICABILITY

By providing a novel β-galactoside-α2,6-sialyltransferase and a nucleic acid encoding the same, the present invention provides a means for synthesizing and producing sugar chains which are shown to have important functions in the body. In particular, sialic acid is often located at the nonreducing termini of complex carbohydrate sugar chains in the body and is a very important sugar in terms of sugar chain functions. Thus, sialyltransferase is one of the most in demand enzymes among glycosyltransferases. The novel sialyltransferase of the present invention can be used for the development of pharmaceuticals, functional foods and other products where sugar chains are applied.

The invention claimed is:

1. An isolated protein having β-galactoside-α2,6-sialyltransferase activity, which comprises:
   (a) an amino acid sequence selected from the group consisting of SEQ ID NO: 2, SEQ ID NO: 4, and amino acids 16-497 of SEQ ID NO: 2; or
   (b) an amino acid sequence comprising an amino acid sequence identity of 90% or more with an amino acid sequence selected from the group consisting of SEQ ID NO: 2, SEQ ID NO: 4, and amino acids 16-497 of SEQ ID NO: 2.

2. An isolated protein having β-galactoside-α2,6-sialyltransferase activity, which is encoded by a nucleic acid comprising:
   (a) a nucleotide sequence selected from the group consisting of SEQ ID NO: 1, SEQ ID NO: 3, and nucleotides 46-1494 of SEQ ID NO: 1;
   (b) a nucleotide sequence comprising a sequence identity of 90% or more with a nucleotide sequence selected from the group consisting of SEQ ID NO: 1, SEQ ID NO: 3, and nucleotides 46-1494 of SEQ ID NO: 1; or,
   (c) a nucleotide sequence hybridizable under a hybridization condition of 65° C., 6×SSC, and a washing condition of 65° C., 0.2×SSC, 0.1% SDS with the complementary strand of a nucleotide sequence selected from the group consisting of SEQ ID NO: 1, SEQ ID NO: 3, and nucleotides 46-1494 of SEQ ID NO: 1.

3. The isolated protein according to claim 1 or 2, which is obtained from a microorganism belonging to the genus *Photobacterium*.

4. The isolated protein according to claim 1 or 2, which has an optimum reaction pH ranging from pH 7 to pH 9.5.

5. A method for increasing the efficiency of glycosyltransfer reaction mediated by the β-galactoside-α2,6-sialyltransferase of claim 1, wherein the reaction is carried out in the presence of a monovalent metal ion to thereby increase the reaction efficiency when compared to the absence of the monovalent metal ion.

6. The method of claim 5, wherein the monovalent metal ion is sodium ion, potassium ion or lithium ion.

7. A method for increasing the efficiency of glycosyltransfer reaction mediated by the β-galactoside-α2,6-sialyltransferase of claim 1, wherein the reaction is carried out in the presence of an anion selected from the group consisting of phosphate ion, sulfate ion, nitrate ion, borate ion, chloride ion, fluoride ion and any combination thereof to thereby increase the reaction efficiency when compared to the absence of the anion.

8. A method for increasing the efficiency of glycosyltransfer reaction mediated by the β-galactoside-α2,6-sialyltransferase of claim 1, wherein the reaction is carried out in the presence of a salt formed between a monovalent metal ion and an anion selected from the group consisting of phosphate ion, sulfate ion, nitrate ion, borate ion, chloride ion and fluoride ion to thereby increase the reaction efficiency when compared to the absence of the salt.

9. A method for increasing the efficiency of glycosyltransfer reaction mediated by the β-galactoside-α2,6-sialyltransferase of claim 1, wherein the reaction is carried out in the presence of calcium ion to thereby increase the reaction efficiency when compared to the absence of calcium ion.

10. A method for increasing the efficiency of glycosyltransfer reaction mediated by the β-galactoside-α2,6-sialyltransferase of claim 1, wherein the reaction is carried out in the presence of a salt formed between calcium ion and an anion selected from the group consisting of phosphate ion, sulfate ion, nitrate ion, borate ion, chloride ion and fluoride ion to thereby increase the reaction efficiency when compared to the absence of the salt.

* * * * *